US009725742B2

(12) United States Patent
Escudero et al.

(10) Patent No.: US 9,725,742 B2
(45) Date of Patent: Aug. 8, 2017

(54) HIGH EFFICIENCY ETHANOL PROCESS AND HIGH PROTEIN FEED CO-PRODUCT

(71) Applicant: Abengoa Bioenergy New Technologies, LLC, Chesterfield, MO (US)

(72) Inventors: Carlos Blázquez Escudero, Chesterfield, MO (US); Pablo Gutiérrez Gómez, Chesterfield, MO (US)

(73) Assignee: Abengoa Bioenergy New Technologies, LLC, Chesterfield, MO (US)

( * ) Notice: Subject to any disclaimer, the term of this patent is extended or adjusted under 35 U.S.C. 154(b) by 69 days.

(21) Appl. No.: 14/399,630

(22) PCT Filed: May 9, 2013

(86) PCT No.: PCT/US2013/040356
§ 371 (c)(1),
(2) Date: Nov. 7, 2014

(87) PCT Pub. No.: WO2013/170034
PCT Pub. Date: Nov. 14, 2013

(65) Prior Publication Data
US 2015/0118727 A1    Apr. 30, 2015

Related U.S. Application Data

(60) Provisional application No. 61/645,218, filed on May 10, 2012.

(51) Int. Cl.
| C12P 7/06 | (2006.01) |
| C12P 7/14 | (2006.01) |
| C12P 7/10 | (2006.01) |
| C12P 19/14 | (2006.01) |
| C07C 29/80 | (2006.01) |
| A23K 10/38 | (2016.01) |

(52) U.S. Cl.
CPC ............... *C12P 7/14* (2013.01); *A23K 10/38* (2016.05); *C07C 29/80* (2013.01); *C12P 7/06* (2013.01); *C12P 7/10* (2013.01); *C12P 19/14* (2013.01); *C12P 2201/00* (2013.01); *C12P 2203/00* (2013.01); *Y02E 50/16* (2013.01); *Y02P 60/873* (2015.11)

(58) Field of Classification Search
CPC ......... C12P 7/10; C12P 19/14; C12P 2201/00; C12P 7/14; Y02E 50/16; C07C 29/80; Y02P 60/873; A23K 10/38
See application file for complete search history.

(56) References Cited

U.S. PATENT DOCUMENTS

| 3,236,740 A | 2/1966 | Smith et al. |
| 4,200,692 A | 4/1980 | Puls et al. |
| 4,376,163 A | 3/1983 | Ehnstrom |
| 4,752,579 A | 6/1988 | Arena et al. |
| 4,806,475 A | 2/1989 | Gould |
| 4,822,737 A | 4/1989 | Saida |
| 5,047,332 A | 9/1991 | Chahal |
| 5,177,008 A | 1/1993 | Kampen |
| 5,487,989 A | 1/1996 | Fowler et al. |
| 5,705,369 A | 1/1998 | Torget et al. |
| 5,733,758 A | 3/1998 | Nguyen |
| 5,932,452 A | 8/1999 | Mustranta et al. |
| 6,090,595 A | 7/2000 | Foody et al. |
| 6,444,437 B1 | 9/2002 | Sporleder et al. |
| 6,569,653 B1 | 5/2003 | Alard et al. |
| 6,927,048 B2 | 8/2005 | Verser et al. |
| 2003/0044951 A1 | 3/2003 | Sporleder et al. |
| 2006/0233864 A1 | 10/2006 | Power |
| 2007/0037267 A1 | 2/2007 | Lewis et al. |
| 2007/0218530 A1 | 9/2007 | Duck et al. |
| 2007/0250961 A1 | 10/2007 | Blaylock et al. |
| 2009/0093027 A1* | 4/2009 | Balan .................. C12P 7/10 435/99 |
| 2011/0008489 A1 | 1/2011 | Robb et al. |

FOREIGN PATENT DOCUMENTS

| CN | 1151834 A | 6/1997 |
| CN | 1208077 A | 2/1999 |

(Continued)

OTHER PUBLICATIONS

Tory-Smith M. "Fast fermentation of C5 and C6 sugars in lignocellulosic hydrolysates", Novozyme webinar series, Jun. 2009, published on web at—http://www.bioenergy.novozymes.com/en/learn-more/webinars/Documents/FastFermC5C6Webinar.pdf; total pp. 1-25.*
Voegele E. "Microbiogen develops yeast that can utilize both C5, C6 sugars", published on web on Aug. 25, 2009 at—http://biomassmagazine.com/articles/3016/microbiogen-develops-yeast-that-can-utilize-both-c5-c6-sugars, total p. 1.*
Al-Suwaiegh, S., et al., "Utilization of Distillers Grains from the Fermentation of Sorghum or Corn in Diets for Finishing Beef and Lactating Dairy Cattle," J Anim Sci, 2002, vol. 80, pp. 1105-1111.
Armentano, L., "How Can We Optimize the Protein Quality Delivered to Lactating Cows When Feeding DDGS?," Proceedings Distillers Feed Research Council, 1994, pp. 63-68.

(Continued)

*Primary Examiner* — Satyendra K Singh
(74) *Attorney, Agent, or Firm* — Armstrong Teasdale LLP

(57) ABSTRACT

A process for obtaining high ethanol yield from the fermentation of an energy crop and for producing a nutritionally enhanced feed co-product is provided. In particular, the process includes converting non-fermentable polysaccharides in an energy crop into fermentable sugar. The fermentable sugars may be fermented into ethanol thereby enhancing the ethanol yield. In addition, separation of ethanol from the fermentation product yields a whole stillage product having enhanced protein content and reduced fiber content. The process requires little or no modification to the configuration of existing commercial ethanol facilities.

20 Claims, 1 Drawing Sheet

(56) References Cited

FOREIGN PATENT DOCUMENTS

| WO | 0238787 | A2 | 5/2002 |
|---|---|---|---|
| WO | 2004018645 | A2 | 3/2004 |
| WO | 2004081193 | A2 | 9/2004 |
| WO | 2004103086 | A2 | 12/2004 |
| WO | 2005079190 | A2 | 9/2005 |
| WO | 2009079183 | A1 | 6/2009 |
| WO | 2011056991 | A1 | 5/2011 |

OTHER PUBLICATIONS

Armentano, L.E., "Altered Milk Production Due to Changes in Protein Quality for Diets Based on Distillers Dried Grains with Solubles,"J. Anim. Sci., vol. 72, Suppl. 1 / J. Dairy Sci., vol. 77, Suppl. 1, 1994, p. 244.

De Menezes, T.J.B., "The Treatment and Utilization of Alcohol Stilllage," International Biosystems, vol. III, D.L. Wise, editor, 1989, CRC Press, Inc. Boca Raton, Florida, USA, pp. 1-14.

Dien, B.S., et al., "Conversion of Corn Fiber to Ethanol by Recombinant E. Coli Strain FBR3," Journal of Industrial Microbiology Biotechnology, 1999, vol. 22 , pp. 575-581.

Elander, R.T., "Executive Summary New Energy Company of Indiana/National Renewable Energy Lab (NREL) Co-Op Research and Development Agreement (CRADA) Completed 1997," Public Release 1999, NREL, Golden, Colorado, USA, 11 pages.

Ghose, T.K., "Measurement of Cellulase Activities," Pure and Appl Chem, 1987, vol. 59, No. 2, pp. 257-268.

Gulati, M., et al., "Assessment of Ethanol Production Options for Corn Products," Bioresource Technology, 1996, vol. 58, pp. 253-264.

Irwin, D., et al., "Corn Fiber Hydrolysis by Themobifida Fusca Extracellular Enzymes," Appl Microbiol Biotechnol, 2003, vol. 61, pp. 352-358.

Lardy, G., "Feeding Coproducts of the Ethanol Industry to Beef Cattle," NDSU Extension Service, 2007, 8 pages.

Leathers, T.D., "Bioconversions of Maize Residues to Value-Added Coproducts Using Yeast-like Fungi," FEMS Yeast Research, 2003, vol. 3, pp. 133-140.

Liu, C., et al., "Corn Distillers Grains versus a Blend of Protein Supplements with or without Ruminally Protected Amino Acids for Lactating Cows," J Dairy Sci, 2000, vol. 83, pp. 2075-2084.

Nichols, J.R., et al., "Evaluation of Corn Distillers Grains and Ruminally Protected Lysine and Methionine for Lactating Dairy Cows," J Dairy Sci, 1998, vol. 81, pp. 482-491.

Reeve, A., "Chapter 4 Starch Hydrolysis: Processes and Equipment," Starch Hydrolysis Products Worldwide Technology, Production, and Applications, F.W. Schenck and R. E. Hebeda, editors, VCH (Wiley), New York, New York, USA, 1992, pp. 79-120.

Schingoethe, D.J., et al., "Milk Production and Composition from Cows Fed Wet corn Distillers Grains," J. Dairy Sci, 1999, vol. 82, pp. 574-580.

Singh, V., et al., "A Comparison Between Conversion of Pericarp and Endosperm Fiber from Corn into Ethanol," Paper No. 046056, ASAE Annual Meeting, 2004, 15 pages.

Teleman, A., et al., "Progress-Curve Analysis Shows that Glucose Inhibits the Cellotriose Hydrolysis Catalysed by Cellobiohydrolase II from Trichoderma Reesei," Eur J Biochem, 1995, vol. 231, pp. 250-258.

Wilkie, A.C., et al., "Stillage Characterization and Anaerobic Treatment of Ethanol Stillage from Conventional and Cellulosic Feedstocks," Biomass & Bioenergy, 2000, vol. 19, pp. 63-102.

Wu, Y.V., "Protein-Rich Residue from Ethanolic Fermentation of High-Lysine, Dent, Waxy, and White Corn Varieties," Cereal Chem, 1989, vol. 66, No. 6. pp. 506-509.

European Search Report and European Search Opinion issued in related European Patent Application No. 10829102.2 dated Nov. 30, 2012; 10 pages.

International Search Report and Written Opinion for corresponding International Application No. PCT/US10/55478, dated Mar. 11, 2011, 15 pages.

International Search Report and Written Opinion for corresponding International Application No. PCT/US2013/040356, dated Oct. 25, 2013, 14 pages.

"Liquozyme SC DS—Take Your Liquefaction to New Levels", Available online at www.bioenergy.novozymes.com on Aug. 22, 2007, 3 pgs.

* cited by examiner

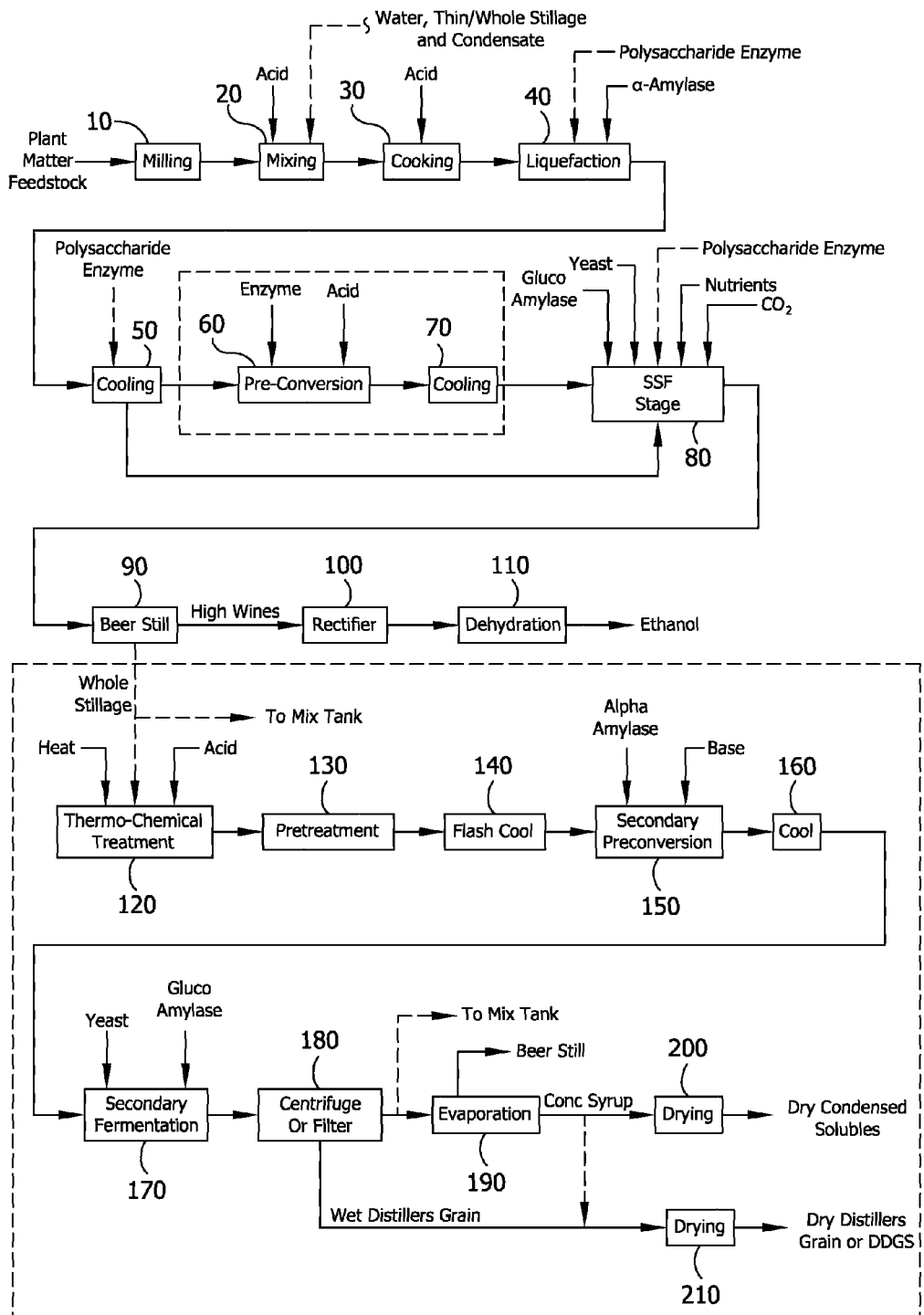

HIGH EFFICIENCY ETHANOL PROCESS AND HIGH PROTEIN FEED CO-PRODUCT

REFERENCE TO RELATED APPLICATIONS

This application is a United States National Stage Application based on International Patent Application Number PCT/US2013/040356, filed May 9, 2013, and claims the benefit of U.S. Provisional Patent Application Ser. No. 61/645,218, filed May 10, 2012, the entire contents of which are incorporated herein by reference.

FIELD OF THE INVENTION

The present invention relates to a process for obtaining high ethanol yield from the fermentation of an energy crop and for producing a nutritionally enhanced feed co-product. The process includes converting non-fermentable polysaccharides in an energy crop into fermentable sugar, which then may be fermented into ethanol thereby enhancing ethanol yield.

BACKGROUND OF THE INVENTION

Ethanol and corresponding feed co-products may be produced from a variety of feedstocks using any conventional dry mill or wet mill fermentation process known in the art. See for example, CORN, Chemistry and Technology, Stanley A. Watson and Paul E. Ramstad, editors, Published by the American Association of Cereal Chemists, Inc., St. Paul, Minn., USA, the entire contents of which are incorporated herein by reference.

Maximizing ethanol output is a concern for owners and operators of existing ethanol facilities. Thus, there exists a need for cost-effective measures that increase ethanol output from ethanol facilities, particularly from cereal based facilities.

Ethanol produced from fermentation of cereal grains yields co-products that are useful as animal feeds. Some of these feed co-products are known in the art as Wet Distiller's Grains (WDG), Dried Distiller's Grains (DDG), Wet Distiller's Grains Plus Solubles (WDGS), or Dried Distiller's Grains plus Solubles (DDGS). Removal of the starch component during fermentation concentrates the original protein, mineral, vitamin, fiber, and fat content. For example, dry mill ethanol production uses the starch portion of corn kernels, which is about 70% of the kernel. The starch component is converted by enzymatic hydrolysis to sugars which are then fermented to form ethanol. The ethanol is recovered by distillation. The remaining nutrients are concentrated into WDG or WDGS. The WDG or WDGS may be used directly as a feed co-product or may be dried to form DDG or DDGS. Drying increases shelf life and improves transportability.

Among the grain feed components, protein has the highest value commercially while fiber has the least value. Although the nutritional value of grain feed products may vary slightly according to its source (e.g., corn, sorghum (milo), sugar beets) and crop quality, these are essentially commodity products. Accordingly, a method for improving the quality and value (i.e., increased protein content and/or decreased fiber content) of grain feed co-products resulting from ethanol production is desirable to produce grain feed products having enhanced nutritional value as compared to the grain feed products currently available from the commodity markets.

SUMMARY OF THE INVENTION

Briefly, therefore, the present invention is directed to a process for producing ethanol. In various embodiments, the process comprises forming an acidic aqueous medium comprising a plant matter feedstock and having a pH of from about 2 to about 6, wherein the plant matter comprises starch and another polysaccharide selected from the group consisting of cellulose, hemicellulose, and combinations thereof, and hydrolyzing at least a portion of the starch, the another polysaccharide, or both in the acidic aqueous medium at a temperature of at least about 85° C. The process further comprises contacting at least a portion of the starch in the acidic aqueous medium with an α-amylase, which catalyzes enzymatic hydrolysis of at least a portion of the starch to yield an enzymatic hydrolysate containing simple sugars having from one to three saccharide units. The process also comprises contacting the enzymatic hydrolysate in a simultaneous saccharification-fermentation (SSF) zone with a yeast, a glucoamylase, and a polysaccharide enzyme selected from the group consisting of cellulase, hemicellulase, and combinations thereof to form a saccharification-fermentation mixture. The polysaccharide enzyme catalyzes the hydrolysis of at least a portion of the another polysaccharide to simple sugars having from one to four saccharide units. During the saccharification-fermentation period at least a portion of the simple sugars derived from the starch are converted by fermentation to produce ethanol within the SSF zone and at least a portion of the simple sugars derived from the another polysaccharide are converted by fermentation to produce ethanol within the SSF zone.

The present invention is further directed to a process for producing ethanol comprising forming an acidic aqueous medium comprising a plant matter feedstock and having a pH of from about 2 to about 6, wherein the plant matter comprises starch and another polysaccharide selected from the group consisting of cellulose, hemicellulose, and combinations thereof, and hydrolyzing at least a portion of the starch, the another polysaccharide, or both in the acidic aqueous medium at a temperature of at least about 85° C. The process also comprises contacting at least a portion of the starch in the acidic aqueous medium in a liquefaction zone with an α-amylase and a polysaccharide enzyme selected from the group consisting of cellulase, hemicellulase, and combinations thereof, wherein the α-amylase catalyzes enzymatic hydrolysis of at least a portion of the starch to yield an enzymatic hydrolysate containing simple sugars having from one to three saccharide units and the polysaccharide enzyme catalyzes the hydrolysis of at least a portion of the another polysaccharide to simple sugars having from one to four saccharide units. Further, the process comprises contacting the enzymatic hydrolysate in a simultaneous saccharification-fermentation (SSF) zone with a yeast and a glucoamylase to form a saccharification-fermentation mixture. During the saccharification-fermentation period at least a portion of the simple sugars derived from the starch are converted by fermentation to produce ethanol within the SSF zone and at least a portion of the simple sugars derived from the another polysaccharide are converted by fermentation to produce ethanol within the SSF zone.

Additionally, the present invention is directed to a process for producing ethanol comprising forming an acidic aqueous medium comprising a plant matter feedstock and having a pH of from about 2 to about 6, wherein the plant matter comprises starch and another polysaccharide selected from the group consisting of cellulose, hemicellulose, and combinations thereof, and hydrolyzing at least a portion of the starch, the another polysaccharide, or both in the acidic aqueous medium at a temperature of at least about 85° C. The process also comprises contacting at least a portion of the starch in the acidic aqueous medium with an α-amylase, which catalyzes enzymatic hydrolysis of at least a portion of the starch to yield an enzymatic hydrolysate containing simple sugars having from one to three saccharide units. Further, the process comprises contacting the enzymatic hydrolysate with a polysaccharide enzyme selected from the group consisting of cellulase, hemicellulase, and combinations thereof and reducing the temperature of the enzymatic hydrolysate in a cooling zone, wherein the polysaccharide enzyme catalyzes the hydrolysis of at least a portion of the another polysaccharide to simple sugars having from one to four saccharide units. Still further, the process comprises contacting the enzymatic hydrolysate obtained from the cooling zone in a simultaneous saccharification-fermentation (SSF) zone with a yeast and a glucoamylase to form a saccharification-fermentation mixture. During the saccharification-fermentation period at least a portion of the simple sugars derived from the starch are converted by fermentation to produce ethanol within the SSF zone and at least a portion of the simple sugars derived from the another polysaccharide are converted by fermentation to produce ethanol within the SSF zone.

Other objects and features will be in part apparent and in part pointed out hereinafter.

BRIEF DESCRIPTION OF THE DRAWINGS

FIG. 1 is a block flow diagram depicting an embodiment of the process of the present invention.

DESCRIPTION OF THE PREFERRED EMBODIMENTS

The present invention generally relates to processes for the production of ethanol by the fermentation of plant matter, particularly energy crops. Advantageously, the present invention provides a process for increasing ethanol yield which requires little or no modification to the configuration of existing commercial ethanol facilities.

In various aspects, the present invention provides a process for increasing the ethanol yield by converting non-fermentable polysaccharides in an energy crop into fermentable sugars. In conventional cereal processes, these complex polysaccharides (e.g., cellulose and hemicellulose) typically provide little or no fermentable sugar substrate to the ethanol fermentation process and remain part of the stillage based co-products. According to the process of the present invention, at least a portion of these complex polysaccharides is converted to fermentable sugars. The fermentable sugars may be fermented into ethanol thereby enhancing the ethanol yield. In addition, separation of ethanol from the fermentation product yields a whole stillage product having enhanced protein content and reduced fiber content.

Further, in other aspects, the present invention provides a process for producing a feed co-product of improved nutritional quality. In particular, the present invention provides a process for producing a modified co-feed product having increased protein content and reduced fiber content. By converting at least a portion of complex polysaccharides of little nutritive value in the plant matter feedstock into fermentable sugars and fermenting at least a portion of the fermentable sugars to produce ethanol, the process of the present invention yields whole stillage and feed co-products derived therefrom comprising enhanced concentrations of the components of high nutritional quality (e.g., protein and oil) and reduced concentrations of complex polysaccharides of little nutritive value (e.g., hemicellulose and cellulose). The present invention is therefore further directed to the feed co-product having enhanced nutritive value as compared to the grain feed products currently available from the commodity markets. Since the nutritionally enhanced feed co-products of the present invention have improved nutritional quality compared to conventional feed co-products, such as conventional dried distiller's grains, it is believed the process of the present invention increases the commercial value of the feed co-product thereby enhancing the profitability of the overall ethanol production process. The feed co-product of the present invention may be utilized as a high quality feed for all animal feed applications. For example, the product of the present invention may be utilized as a feed for mono-gastric animals and may even be used for human consumption.

Plant Matter Feedstocks

The plant matter feedstocks for use in the process of the present invention generally include plant matter derived from an energy crop. As known in the art, an energy crop is a plant whose fruits and/or seeds may be used in the production of biofuels. The fruits and seeds (e.g., corn kernels, wheat berries—with or without the hull, oat groats—with or without the hull, etc.) of energy crops typically contain protein, oil, and complex polysaccharides. More particularly, the primary components are starch, cellulose, hemicellulose, and other fibers, such as lignin-cellulose complex and lignin-hemicellulose complex. Conventionally, starch is the most important energy source in ethanol fermentation. Starch is enzymatically hydrolyzed to glucose, which is converted by yeast into ethanol and carbon dioxide. The fruits and/or seeds of an energy crop typically comprise a large portion of starch, which is readily fermentable into ethanol by conventional processes. The feedstock used in the process of the present invention may be any feedstock comprising at least about 40% by weight, preferably at least about 50% by weight of a carbohydrate, such as a starch or sugar, which is fermentable into ethanol. A corn kernel, for example, typically comprises about 70% by weight starch on a dry basis. Sorghum (milo) also contains about 70% by weight starch. Wheat contains about 65% by weight starch. Rye contains about 58% by weight starch. Barley contains about 51% by weight starch.

Plant matter feedstocks derived from the Poaceae family (the "true grasses") comprise the fruits and/or seeds of cereal grains including corn, maize, oats, grain sorghum, milo, wheat, barley, triticale, rice, millet, rye, and buckwheat. Additional true grasses include bamboo, marram grass, meadow grass, reed, ryegrass, sugar cane, and grasses from the *Miscanthus* genus. The plant matter feedstocks may also be derived from tubers, including potatoes, cassava, sweet potato, and yam.

Plant matter feedstocks may be derived from the Amaranthaceae family, including sugar beet, amaranth, and quinoa. Other plant matter feedstocks include willows from the *Salix* genus and flowering plants from the *Populus* genus, both classified in the Salicaceae family.

In various embodiments, the plant matter feedstock is derived from corn, grain sorghum, wheat, barley, sugarcane, and/or sugar beets, potatoes, and cassava. In some embodiments, the plant matter feedstock comprises corn, wheat, barley or mixtures thereof.

The energy crops for use in the process of the present invention are suitable plant matter feedstocks since they comprise sugars, including starch, and fibers, such as cellulose and hemicellulose that are or may be treated to yield simple sugar substrates suitable for ethanol fermentation. Starches typically comprise two components: amylose and amylopectin. Amylose is a polysaccharide that may comprise up to several thousand glucose units, more typically comprising from about 300 to about 3000 glucose units in alpha linkages. Amylose is characterized by relatively little branching, such that the main linkage is α(1→4), which promotes formation of a helical structure. Amylopectin is a polysaccharide typically comprising from about 2000 to about 20,000 glucose units in alpha linkages. Unlike amylose, amylopectin is highly branched and comprises linear portions in α(1→4) linkages with branching taking place through α(1→6) linkages about every 24 to 30 glucose units. Plants store amylopectin and amylose as starch granules in amyloplasts. Certain varieties of plants are "waxy," meaning that the starch granules have no amylose.

Cellulose is a structural, linear polysaccharide of the plant cell wall, which contains anywhere from several hundred to over ten thousand glucose units in β(1→4) linkages. Cellulose is a major component of energy crops. Hemicelluloses are heteropolymers also present in cell walls, and its polysaccharides include glucose, xylose, mannose, galactose, rhamnose, and arabinose. Since hemicellulose is a random, amorphous polymer, it provides little strength and is easily hydrolyzed by dilute acid or base and a variety of hemicellulase enzymes. Hemicellulose typically comprises about 200 saccharide units. Hemicellulose include xylan, glucuronoxylan, arabinoxylan, glucomannan, and xyloglucan. Hemicellulose is covalently linked to lignin, a complex, cross-linked, polymeric macromolecule that fills the spaces in cell walls between the cellulose, hemicellulose, and pectin components.

Process for Production of Ethanol

In accordance with the present invention, processes for producing ethanol are provided. Generally, the processes are multistage and include forming an acidic aqueous medium comprising a plant matter feedstock and having a pH of from about 2 to about 6, wherein the plant matter comprises starch and another polysaccharide selected from the group consisting of cellulose, hemicellulose, and combinations thereof. Also, the processes include hydrolyzing at least a portion of the starch, the another polysaccharide, or both in the acidic aqueous medium at a temperature of at least about 85° C. Additionally, the processes include contacting at least a portion of the starch in the acidic aqueous medium with an α-amylase, which catalyzes enzymatic hydrolysis of at least a portion of the starch to yield an enzymatic hydrolysate containing simple sugars having from one to three saccharide units. Further, the processes include contacting the enzymatic hydrolysate in a simultaneous saccharification-fermentation (SSF) zone with a yeast and a glucoamylase.

Generally, the processes include catalyzing the hydrolysis of at least a portion of the another polysaccharide to simple sugars having from one to four saccharide units by introducing a polysaccharide enzyme selected from the group consisting of cellulase, hemicellulase, and combinations thereof. In various embodiments, at least a portion of the enzymatic hydrolysate is contacted with a polysaccharide enzyme in the SSF zone. In other embodiments, at least a portion of the acidic aqueous medium is contacted with a polysaccharide enzyme in the liquefaction zone. In some embodiments, at least a portion of the enzymatic hydrolysate is contacted with a polysaccharide enzyme and the temperature of the enzymatic hydrolysate is reduced in a cooling zone, which is downstream of the liquefaction zone. Further, during the saccharification-fermentation period at least a portion of the simple sugars derived from the starch are converted by fermentation to produce ethanol within the SSF zone and at least a portion of the simple sugars derived from the another polysaccharide are converted by fermentation to produce ethanol within the SSF zone.

An embodiment of the process of the present invention is generally depicted in FIG. 1.

Milling

Preferably, the plant matter feedstock is storage grain which has been dried to an extent that inhibits microbial action (i.e., spoilage) and allows for long term storage. Typically, the raw plant matter feedstock derived from the fruit and/or seed of the energy crop (such as a corn, wheat, or barley grain in various embodiments) is dry milled or wet milled in milling zone 10. The plant matter feedstock for use in the process of the present invention may be dry milled or wet milled to a very fine particle size.

In a dry milling operation, the raw plant matter (i.e., the seed and/or fruit of the energy crop), for example, the entire corn kernel, is first ground, typically using a hammer mill and screens, into flour, which is referred to in the industry as "meal" and processed without separating out the various component parts of the grain. The industry has preferred milling to a relatively coarse grain since it is thought that cooking is sufficient to paste the starch and a coarser grain yields a whole stillage product that is easier to separate into thin stillage and the wet cake. However, finely milled flour enhances the overall conversion of starch into ethanol and is not detrimental to the separation of thin stillage from the wet cake. In some embodiments, the grain is dry milled into a flour or meal having particle sizes ranging from about 250 micrometers to about 1200 micrometers, preferably ranging from about 500 micrometers to 750 micrometers. As stated above, after dry milling, the flour comprises all of the grain components, including the protein, starch, fibers, and oil. In some embodiments, the raw plant matter feedstock is finely milled flour from dry milling.

In wet milling, the grain is first soaked or steeped in sulfurous acid to soften the grains and allow wet grinding to release the oil-containing germ and coarse fiber from the endosperm. The fiber and germ are separated and the endosperm further processed and separated into starch and protein fractions in some wet milling applications. The separated starch streams from a wet-mill can advantageously serve as a feedstock to the ethanol fermentation process due to the reduced amount of non-fermentable matter entering the process and the ability to capture the oil, protein, and fiber separately which have economic value for human food and other applications. See, McFate, U.S. Pat. No. 3,236,740. Wet milling is preferably done to a fine grind in order to enhance the separation of protein from starch in grains in the cooking step.

Mixing

Referring back to FIG. 1, the dry or wet milled plant matter feedstock is combined with aqueous liquid and, optionally, an acid in mixing zone 20 to form an acidic aqueous medium (i.e., mash). The liquid may be water, recycled whole stillage, a recycled whole stillage condensate, recycled thin stillage, a recycled thin stillage condensate, or combinations thereof, wherein the whole stillage, thin stillage, condensates of whole stillage, condensates of thin stillage being feed co-products derived from the fermentation of plant matter in a prior ethanol production process. Acidic adjustment is optional and may be performed in order to adjust the pH of the aqueous medium to the desired acidic pH. In some embodiments of the present invention, the acidic aqueous mixture, i.e., mash, is formed by combining a milled plant matter feedstock, i.e., flour from the milling process, water, and recycled whole stillage.

Whole stillage may comprise between about 8% and about 20% dry matter by weight, more typically between about 9.5% and about 14% dry matter by weight, more typically between about 12% and about 14% dry matter by weight. Whole stillage is typically derived from the fermentation of the grain of an energy crop and typically comprises a portion of residual starch that was not fermented by yeast into ethanol. Whole stillage from a prior batch may be recycled into the process of the present invention. By using whole stillage backset to prepare the mash for acid hydrolysis, jet cooking, and fermentation, the process of the present invention enhances the conversion of starch into alcohol, thereby improving ethanol yield per unit mass of plant feedstock.

In these embodiments, the mash comprises flour, whole stillage recycle, and water. The mash may be formulated to comprise between about 25 pounds and about 45 pounds of flour per 100 pounds of mash, preferably between about 30 pounds and about 39 pounds of flour per 100 pounds of mash. In International Standard units (metric), the mash may be formulated to comprise between about 25 kilograms and about 45 kilograms of flour per 100 kilograms of mash, preferably between about 30 kilograms and about 39 kilograms of flour per 100 kilograms of mash. The mash may comprise between about 5 pounds and about 50 pounds of whole stillage per 100 pounds of mash, preferably between about 10 pounds and about 40 pounds of whole stillage per 100 pounds of mash. In International Standard units (metric), the mash may comprise between about 5 kilograms and about 50 kilograms of whole stillage per 100 kilograms of mash, preferably between about 10 kilograms and about 40 kilograms of whole stillage per 100 kilograms of mash. The mash may comprise between about 30 pounds and about 70 pounds of water per 100 pounds of mash, preferably between about 35 pounds and about 55 pounds of water per 100 pounds of mash. In International Standard units (metric), the mash may comprise between about 30 kilograms and about 70 kilograms of water per 100 kilograms of mash, preferably between about 35 kilograms and about 55 kilograms of water per 100 kilograms of mash.

The process of the invention may also be a continuous process, in which process down streams (e.g., whole stillage, thin stillage, condensates of whole stillage and/or condensates of thin stillage) are continuously recycled into the mash.

In some embodiments, the mash is formed by mixing flour, water, whole stillage, and thin stillage. Thin stillage is obtained by the separating coarse solids (i.e., the wet distiller's grains, which contains between about 25% dry matter by weight and about 35% dry matter by weight) from the aqueous portion of whole stillage by, for example, centrifugation. Thin stillage typically comprises about 5% dry matter (solubles) by weight. Condensates of whole stillage may also be recycled into the process at this zone, including modified wet distiller's grains plus solubles having about 50% dry matter by weight and wet distiller's grains plus solubles having about 25 to 35% dry matter by weight. Condensates of thin stillage known as condensed distiller's solubles having from 23 to 45% dry matter by weight may also be recycled into the process at this stage. Finally, even dried distiller's grains or dried distiller's grains plus solubles may be recycled to form the mash in the process of the present invention.

The relative proportions of the components of the mash, i.e., dry milled or wet milled feedstock, water, and, optionally, recycled whole stillage, thin stillage, condensates of whole stillage, or condensates of thin stillage are typically selected such that the mash comprises between about 15% dry matter by weight and about 45% dry matter by weight, more preferably between about 20% dry matter by weight and about 40% dry matter by weight, more preferably between about 30% dry matter by weight and about 37% dry matter by weight. In some embodiments, the mash comprises about 32% dry matter by weight. In other embodiments, the mash comprises about 35% dry matter by weight. In various embodiments, lower amounts of dry matter result in high ethanol yields, such as between about 15% dry matter by weight and about 25% dry matter by weight, such as about 18% dry matter by weight or about 20% dry matter by weight.

In these embodiments, the mash may comprise between about 20 pounds and about 50 pounds of flour per 100 pounds of mash, preferably between about 30 pounds and about 45 pounds of flour per 100 pounds of mash. In International Standard units (metric), the mash may comprise between about 20 kilograms and about 50 kilograms of flour per 100 kilograms of mash, preferably between about 30 kilograms and about 45 kilograms of flour per 100 kilograms of mash. The mash may comprise between about 0 pounds and about 50 pounds of whole stillage per 100 pounds of mash, preferably between about 10 pounds and about 35 pounds of whole stillage per 100 pounds of mash. In International Standard units (metric), the mash may comprise between about 0 kilograms and about 50 kilograms of whole stillage per 100 kilograms of mash, preferably between about 10 kilograms and about 35 kilograms of whole stillage per 100 kilograms of mash. The mash may comprise between about 0 pounds and about 20 pounds of thin stillage per 100 pounds of mash, preferably between about 0 pounds and about 10 pounds of thin stillage per 100 pounds of mash. In International Standard units (metric), the mash may comprise between about 0 kilograms and about 20 kilograms of thin stillage per 100 kilograms of mash, preferably between about 0 kilograms and about 10 kilograms of thin stillage per 100 kilograms of mash. The mash may comprise between about 30 pounds and about 65 pounds of water per 100 pounds of mash, preferably between about 35 pounds and about 60 pounds of water per 100 pounds of mash. In International Standard units (metric), the mash may comprise between about 30 kilograms and about 65 kilograms of water per 100 kilograms of mash, preferably between about 35 kilograms and about 60 kilograms of water per 100 kilograms of mash.

The mash is typically agitated, such as by paddle stirring, stir plate, vortex, or shaker, with heating, typically to a temperature below the gelation point of starch, such as between about 45° C. and about 65° C.

Cooking

Again, referring back to FIG. 1, an acidic aqueous medium comprising the plant matter feedstock may be formed by cooking the mash in cooking zone 30 by heating the fluid mixture using, for example, steam injection. Heating pastes the starch by breaking up starch crystals and hydrating the starch granules (i.e., gelatinization), which promotes acid hydrolysis of at least a portion of the starch, the cellulose, and/or the hemicellulose into simpler sugars, i.e., oligomers, $C_6$ and $C_5$ monosaccharides, disaccharides, trisaccharides, etc. Acid hydrolysis also separates lignin from lignin-cellulose and lignin hemicellulose complexes. In this zone of the process, the aqueous medium comprising plant matter containing complex polysaccharides including starch, cellulose, and hemicellulose is subjected to acid hydrolysis under generally mild conditions of pH and temperature. To prepare the mash for acid hydrolysis, the pH of the mash may be adjusted to between about 2 and about 6, preferably between about 2 and about 5.5, for example between about 2 and about 4, or at pH such as about 2.5, about 4, or about 5. In some embodiments, the mash may already have a desirable pH within the range of about 2 to about 6. For acidic pH adjustment, if necessary, sulfuric acid and hydrochloric acid are typically used since they are inexpensive, but organic acids, such as acetic acid, lactic acid, citric acid, tartaric acid and the like may be used. If necessary, for alkaline pH adjustment, ammonia is generally used, but other bases, such as sodium hydroxide and potassium hydroxide, are suitable. Some bases are preferably avoided, such as calcium hydroxide since there is a risk that calcium may cause some materials to precipitate. Acid hydrolysis initially occurs at a temperature from about 65° C. to room temperature and more preferably from about 55° C. (which is about the gelation point of starch) to about 45° C. The liquid mash may be agitated by conventional means, such as by paddle stirring, stir plate, vortex, or shaker. Acid hydrolysis may occur under these mild conditions for duration between about five minutes and about 120 minutes.

After a period of mild acidic hydrolysis, the temperature of the aqueous medium may be elevated with indirect heat or more typically, jet cooked with direct steam injection using, for example, a commercial Hydroheater®. The temperature, pressure, and shear forces gelatinizes or 'pastes' the starch (i.e., swells the starch granules with water to hydrate the amylase and amylopectin chains) and render it amenable to enzymatic attack. Jet cooking may further hydrolyze the starch chains. Jet cooking may occur at a temperature of at least about 85° C., or at least about 100° C., such as between about 100° C. and about 200° C., preferably between about 120° C. to about 160° C., such as between about 140° C. to about 160° C. Direct steam injection disperses the aqueous mixture into mist. To disperse the aqueous mixture into mist, the aqueous medium is preferably pumped into the jet cooker at a pressure of at least about 300 kPa (about 45 psi), preferably at least 350 kPa (about 50 psi), more preferably at least 400 kPa (about 58 psi), even more preferably at least about 410 kPa (about 60 psi), and forced through a jet of high velocity steam introduced into the jet cooker at a pressure of at least 800 kPa (about 115 psi), at least 900 kPa (about 130 psi), at least about 1000 kPa (about 145 psi), at least about 1025 kPa (about 148 psi), or at least about 1035 kPa (about 150 psi). The jet cooker preferably has a back pressure of at least about 25 kPa (about 4 psi), at least about 40 kPa (about 6 psi), or even at least about 50 kPa (about 7 psi) or 75 kPa (about 10 psi), as needed, to prevent flashing. In the jet cooker, the pressure of the aqueous mixture drops by between about 200 kPa (about 30 psi) and about 325 kPa (about 50 psi), such as between about 250 kPa (about 35 psi) and about 300 kPa (about 45 psi), such as about 275 kPa (about 40 psi). The pressure of the steam drops by at least about 700 kPa (about 100 psi), preferably at least about 800 kPa (about 115 psi), such as at least about 850 kPa (about 125 psi), or about 900 kPa (about 130 psi). The pressure drop of the steam and the liquid mixture assists in dispersing the fluid mixture into a mist in the jet cooker. The steam swells starch granules, thereby hydrating the granules and destroying their crystalline structure. Jet cooking at elevated temperature may occur for between about 5 minutes and about 20 minutes, preferably about 10 minutes. Typically, the dextrose equivalency (DE) of the medium resulting from jet cooking and acid hydrolysis is between about 1 and about 12.

Jet cooking under acidic conditions solubilizes and gelatinizes the amylose and branched amylopectin chains of the starch and makes them available for further enzymatic hydrolysis. Moreover, jet cooking thins the material at the temperature at which the material is introduced into the enzymatic reactor. The acidic conditions also hydrolyze at least a portion of the amylose and amylopectin, yielding glucose oligomers. The acidic conditions also serve to condition the cell walls and further enhance the release and availability of the starch. In addition, the acidic condition and temperature in the cooking step breaks down lignin-hemicellulose complexes and may hydrolyze the hemicellulose, thereby producing soluble oligomers and monomers of xylose and arabinose and other sugars.

Liquefaction

Referring back to FIG. 1, after forming an acidic aqueous medium (pH from about 2 to about 6) comprising the plant matter feedstock and hydrolyzing at least a portion of the starch, another polysaccharide (cellulose or hemicellulose), or both in the acidic aqueous medium at a temperature of at least about 85° C. in the cooking zone, this acidic aqueous medium (i.e., cooked mash) is then cooled and combined with an α-amylase enzyme in liquefaction zone 40 to form a liquefied enzymatic hydrolysate, wherein the α-amylase enzyme catalyzes enzymatic hydrolysis of at least a portion of the starch to form simple sugars, such as glucose, maltose, maltotriose, limit dextrins, etc.

In this zone, a thermally stable α-amylase enzyme is added to the aqueous medium comprising gelatinized starch to liquefy it. α-Amylase hydrolyzes the starch chains solubilized by acid hydrolysis and cooking to short non-retrograding versions and lowers the viscosity of the liquefied medium. Retrogradation is recrystallization that occurs during cooling, which makes starch resistant to fermentation. α-Amylase acts at random locations along the starch chain and breaks down long-chain carbohydrates, ultimately yielding non-retrograding sugars, such as maltotriose and maltose from amylose (reduction of amylose can be measured using iodine staining), or maltose, glucose, maltodextrins, "limit dextrin" (low MW carbohydrates containing the α(1→6) linkages, which are not hydrolyzed by α-amylase) from amylopectin. α-Amylase enzyme is available commercially, such as from Novozymes, Liquozyme, CDS, Genencor, among other sources. The gelatinization of the prior step solubilizes starches and, to some extent, breaks the starch components down into lower molecular weight oligomers.

Prior to inoculation of the aqueous medium comprising gelatinized starch with the thermally stable α-amylase enzyme, the mixture is cooled to a temperature between about 70° C. and about 90° C., preferably about 85° C., which is an optimal temperature for the α-amylase enzyme catalyzed hydrolysis reaction. The gelatinized medium may optionally be flashed cooled to the desired temperature. If necessary, the pH of the gelatinized medium is adjusted to between about 4 and about 6.5, preferably between about 4.5 and about 6.5, more preferably between about 5 and about 6.5, such as about 5.8. Typically, the pH is adjusted using ammonia, but other bases may be used, such as sodium hydroxide and potassium hydroxide. Some bases are preferably avoided, such as calcium hydroxide since there is a risk that calcium may cause some materials to precipitate. For acidic pH adjustment, if necessary, sulfuric acid and hydrochloric acid are typically used since they are inexpensive, but organic acids, such as acetic acid, lactic acid, citric acid, tartaric acid and the like may be used.

To initiate liquefaction, the gelatinized medium is inoculated with α-amylase typically to a concentration between about 0.02% and about 0.15% based on the dry weight of the solids and more preferably between about 0.04% and about 0.07%, based on the dry weight of the solids. α-Amylase inoculation may occur by batchwise or continuous addition. The gelatinized medium may be inoculated in a vessel that may be a holding tank for batchwise addition. The vessel may be a stretch of pipe that allows plug-flow of the medium during continuous α-amylase inoculation. The relative rates of flow of α-amylase and mash are controlled so that the composition in the mixture is maintained within the preferred range of initial conditions. The enzyme inoculate is allowed to liquefy the mixture for a duration typically between about one and about four hours, preferably about three hours, which is generally sufficient to achieve a dextrose equivalent (DE) in the range of about 10 to about 30, such as about 10 to about 20, more typically between about 12 to about 15.

In various embodiments, the acidic aqueous medium in the liquefaction zone is also contacted with a polysaccharide enzyme selected from the group consisting of cellulase, hemicellulase, and combinations thereof which catalyzes the hydrolysis of at least a portion of the another polysaccharide to simple sugars having from one to four saccharide units. Suitable cellulases and hemicellulases and doses thereof are described further below. Addition of polysaccharide enzymes into the liquefaction zone beneficially provides additional fermentable sugars that may be subsequently fermented into ethanol thereby enhancing ethanol yield. Further, the addition of these enzymes to the liquefaction zone allows such embodiments of the present invention to be implemented in existing ethanol production plants with little or no modification to and investment in the plant. Further, few or no operational changes to the liquefaction process conditions are necessary.

Liquefaction typically occurs at elevated temperatures. Therefore, in some embodiments, following liquefaction at least a portion of the liquefied enzymatic hydrolysate is cooled in cooling zone 50. Typically the temperature of liquefied enzymatic hydrolysate is reduced in the cooling zone to a temperature of from about 35° C. to about 55° C., from about 40° C. to about 55° C., or from about 45° C. to about 55° C. (e.g., about 50° C.), for example, by passage through a heat exchanger or series of heat exchangers.

In other embodiments of the present invention, the enzymatic hydrolysate obtained from the liquefaction zone is contacted with a polysaccharide enzyme selected from the group consisting of cellulase, hemicellulase, and combinations thereof and the temperature of the enzymatic hydrolysate is reduced in a cooling zone. The polysaccharide enzyme(s) catalyze the hydrolysis of at least a portion of the another polysaccharide to simple sugars having from one to four saccharide units. Suitable cellulases and hemicellulases are described further below. The temperature of the enzymatic hydrolysate may be reduced prior to, during, and/or after contact with the polysaccharide enzyme. In certain embodiments, the enzymatic hydrolysate is contacted with the polysaccharide enzyme after the temperature of the enzymatic hydrolysate has been reduced to less than about 65° C., less than about 60° C., less than about 55° C., or less than about 50° C.

Generally, polysaccharide enzymes have a temperature or temperature range activity optimum. Accordingly, in various embodiments the enzymatic hydrolysate is contacted with the polysaccharide enzyme at or near the temperature or within the temperature range activity optimum of the polysaccharide enzyme.

Addition of a polysaccharide enzyme(s) after the liquefaction zone and prior to, during, or after cooling beneficially provides additional fermentable sugars that may be subsequently fermented into ethanol thereby enhancing ethanol yield. Further, the addition of these enzymes prior to, into, and/or after the cooling zone allows this embodiment of the present invention to be implemented in existing ethanol production plants with little or no modification to and investment in the plant. Further, few or no operational changes to the cooling process conditions are necessary.

Optional Pre-Conversion

Referring to FIG. 1, in some embodiments, the liquefied medium from cooling zone 50 may be introduced to optional pre-conversion zone 60 by combining the liquefied medium with a pre-conversion enzyme, which may comprise one or more enzymes, including but not limited to proteases, cellulases, hemicellulases (e.g., xylanases), and combinations of enzymes, which catalyze the enzymatic hydrolysis of cellulose, and hemicellulose (e.g., xylan) to produce simpler sugars, such as oligomers, $C_5$ and $C_6$ sugars, disaccharides, trisaccharides, etc.

Inoculation of the liquefied medium with pre-conversion enzyme may be batchwise or continuous addition. The liquefied medium may be inoculated in a vessel that may be a holding tank for batchwise addition. The vessel may be a stretch of pipe that allows plug-flow during continuous pre-conversion enzyme inoculation. The relative rates of flow of enzyme and liquefied are controlled so that the composition in the mixture is maintained within the preferred range of initial conditions. The liquefied medium is a low viscosity fluid mixture of maltodextrins having a DE ranging from about 10 to about 30 in which the carbohydrate fraction preferably comprises simple sugars, such as glucose, maltose, maltotriose, and maltodextrin products of acid hydrolysis/enzymatic hydrolysis of starch. Acid hydrolysis and enzymatic hydrolysis of hemicellulose yields xylose, arabinose or low molecular weight oligomers thereof.

Primary pre-conversion typically occurs at a temperature between about 35° C. and about 55° C. Moreover, the pH of the liquefied medium is typically between about 4 and about 6.5, preferably between about 4.5 and about 6.5, more preferably between about 5 and about 6.5, such as about 5.8. The pH is typically also appropriate for primary conversion such that pH adjustment is often unnecessary.

To initiate primary pre-conversion, the liquefied medium is inoculated with one or more of the above-described pre-conversion enzymes to a concentration between about 0.001% and about 0.05% based on the dry weight of the solids. Primary pre-conversion may occur for durations up to about 30 hours, preferably between about 2 hours and about 10 hours.

The various enzymes used to inoculate the liquefied medium catalyze hydrolysis of the oligosaccharides, polysaccharides, and proteins in the medium into simpler organic molecules, e.g., five and six carbon monosaccharides, disaccharides, trisaccharides, amino acids, and short peptide chains.

Proteases are added to hydrolyze peptide bonds that link amino acids together in polypeptide chains. Generally any of the classes of proteases are applicable, e.g., acid, base, or neutral, and proteases are commercially available from, for example, Novozymes and Genencor. In general, fine starch granules, particularly from the endosperm, are encased in a protein matrix. Proteases are useful for hydrolyzing the peptide bonds and releasing these starch granules. Moreover, proteases enhance the solubility of proteins, oligopeptides, and amino acids in the mash. Without being bound by a particular theory, it is thought that hydrolysis of the proteins into peptides and amino acids enhances the nutritional value of the final feed co-product, since peptides and amino acids are relatively more soluble than proteins and thus may be more bioavailable in the feed co-product. A commercially available protease that may be used in the process of the present invention is FermGen™, which is an alkaline protease available from Genencor. Also useful is Alcalase®, which is an acid protease available from Novozymes.

Cellulases are a class of enzymes produced chiefly by fungi, bacteria, and protozoans that catalyze the cellulolysis (hydrolysis) of cellulose into glucose, cellobiose, cellotriose, cellotetrose, cellopentose, cellohexose, and longer chain cellodextrins. Combinations of the five basic types of cellulases may be employed. For example, endo-cellulases may be added to disrupt the crystalline structure of cellulose and expose individual cellulose chains. Exo-cellulase may be added to cleave two units (cellobiose), three units (cellotriose), or four units (cellotetrose) from the exposed chains, while beta-glucosidase may be added to hydrolyse these products into glucose, which is available for fermentation. Cellulases are commercially available from such suppliers as Novozymes and Genencor. A commercially available cellulase is GC-220, available from Genencor International.

Hemicellulases may be added to further hydrolyze the various types of hemicelluloses and to further breakdown the products of acid hydrolysis. Xylanases are a subset of hemicellulase enzymes which degrade the linear polysaccharide β-1,4-xylan into xylose (a monosaccharide containing five carbon atoms and including an aldehyde functional group).

Hemicellulases are commercially available from such suppliers as Novozymes and Genencor. Other enzymes may be added to the mash during primary pre-conversion, such as arabinoxylanases and pullulanases. Arabinoxylanases catalyze the hydrolysis of arabinoxylans, yielding arabinose and xylose. Pullulanases are a class of glucanases that catalyze the hydrolysis of amylopectin at the 1→6 bond, thereby yielding oligomers of D-glucose. A commercially available pullulanase is Promozyme® D2, available from Novozyme Corporation. Also useful are multi-enzyme complexes containing multiple carbohydrases, such as Viscozyme® L, available from Novozyme Corporation, which contains arabanase, cellulase, β-glycanase, hemicellulase, and xylanase.

The pre-conversion enzymes catalyze hydrolysis of at least a portion of complex carbohydrates and proteins into simpler molecules, the exact composition of the hydrolysate depending upon the identities of the supplemental enzymes added in to the primary pre-conversion zone.

Following optional pre-conversion, the enzymatic hydrolysate may be cooled in cooling zone 70.

Modified Simultaneous Saccharification and Fermentation (SSF)

Some cereal-based ethanol processes utilize simultaneous saccharification and fermentation (SSF). In conventional SSF, a liquefied cereal feedstock such as corn is contacted with yeast and glucoamylase in the fermentor. Saccharification of starch to fermentable sugars (via glucoamylase) and fermentation of sugars to ethanol (via yeast) occur simultaneously. Applicants have found that conventional SSF in cereal-based ethanol processes may be modified to further include an enzyme capable of catalyzing the hydrolysis of at least a portion of another polysaccharide besides starch (e.g., cellulose and/or hemicellulose) to simple sugars having from one to four saccharide units. Modified SSF according to the present invention beneficially provides additional fermentable sugars that may be fermented into ethanol thereby enhancing ethanol yield.

Modified SSF proceeds, for example as shown in FIG. 1, wherein at least a portion of the enzymatic hydrolysate from liquefaction zone 40, cooling zone 50, and/or cooling zone 70 is introduced to modified SSF zone 80. In this zone, the enzymatic hydrolysate is contacted with a yeast, a glucoamylase, and one or more polysaccharide enzymes selected from the group consisting of cellulase, hemicellulase, and combinations thereof to form a saccharification-fermentation mixture. The polysaccharide enzyme(s) catalyze the hydrolysis of at least a portion of the another polysaccharide (e.g., cellulose and/or hemicellulose) to simple sugars having from one to four saccharide units. During the saccharification-fermentation period at least a portion of the simple sugars derived from the starch of the plant matter feedstock are converted by fermentation to produce ethanol within the SSF zone and at least a portion of the simple sugars derived from the another polysaccharide are converted by fermentation to produce ethanol within the SSF zone.

Prior to, or during SSF, the temperature of the enzymatic hydrolysate may be adjusted to between about 25° C. and about 35° C. (e.g., about 32° C.). Typically, the saccharification-fermentation mixture in the SSF zone is from about 25° C. to about 40° C., from about 25° C. to about 35° C., or from about 30° C. to about 35° C. (e.g., about 32° C.). In various embodiments, the temperature of the enzymatic hydrolysate is reduced prior to contacting with the polysaccharide enzyme. In other embodiments, the temperature of the enzymatic hydrolysate is reduced after contacting with the polysaccharide enzyme. In these and other embodiments, the temperature of the enzymatic hydrolysate is reduced during contact with the polysaccharide enzyme. Moreover, the pH of the saccharification-fermentation mixture may be adjusted and/or maintained from about 4 to about 6.5, from about 4 to about 6, from about 4 to about 5.5, from about 4.5 to about 6, from about 4.5 to about 5.5, or from about 5 to about 6. pH adjustment may occur batchwise or continuously by addition of acid or base to the vessel. The vessel may be a holding tank or a stretch of pipe allowing plug flow of the enzymatic hydrolysate. For acidic pH adjustment, if necessary, sulfuric acid and hydrochloric acid are typically used, but organic acids, such as acetic acid, lactic acid, citric acid, tartaric acid and the like may be used. If necessary, for alkaline pH adjustment, ammonia is generally used, but other bases, such as sodium hydroxide and potassium hydroxide, are applicable. Bases such as calcium hydroxide are generally avoided since there is a risk that calcium may cause some materials to precipitate.

Saccharification and primary ethanol fermentation generally has a duration from about a few days to over a week (saccharification-fermentation period). In various embodiments, the saccharification-fermentation period has a duration of from about 40 to about 100 hours, from about 40 to about 90, from about 40 to about 80, from about 50 to about 100, from about 50 to about 90, from about 50 to about 80, from about 60 to about 100, from about 60 to about 90, or from about 60 to about 80 hours.

In general, the SSF zone may be operated on a continuous, batch, or fed-batch (e.g., including stepwise introduction of feed materials to the zone) basis. The configuration of the reactor(s) in the SSF zone may be readily selected by one skilled in the art. Preferably, the SSF reactors are suitable for continuous, batch or fed-batch operation (e.g., individual or a series of continuous stirred-tank reactors).

In accordance with the present invention, the enzymatic hydrolysate is inoculated with yeast, a glucoamylase, and one or more polysaccharide enzymes (e.g., cellulase and/or hemicellulase). The action of the yeast converts simple $C_6$ sugars (i.e., glucose) into carbon dioxide and ethanol. Conventionally, the yeast species is *Saccharomyces cerevisiae*, but other yeasts that are typically used in fermentation may be used, such as *Saccharomyces carlsbergensis*. The enzymatic hydrolysate may be inoculated with yeast to a concentration of between about $120 \times 10^6$ cells/mL and about $1 \times 10^9$ cells/mL.

Glucoamylase (alternatively known as, γ-Amylase; Glucan 1,4-α-glucosidase; amyloglucosidase; Exo-1,4-α-glucosidase; glucoamylase; lysosomal α-glucosidase; 1,4-α-D-glucan glucohydrolase) serves to cleave any remaining glycosidic linkages for primary ethanol fermentation. In addition to cleaving the last α(1→4) glycosidic linkages at the nonreducing end of amylose and amylopectin, yielding glucose, glucoamylase will cleave α(1→6) glycosidic linkages. The enzymatic hydrolysate may be inoculated with glucoamylase to a concentration of between about 0.02% and about 0.15%, more preferably between about 0.05% and about 0.08%, based on the dry weight of the solids. Various glucoamylases are available commercially, such as from Novozyme.

The polysaccharide enzyme catalyzes the hydrolysis of at least a portion of the another polysaccharide (e.g., cellulose and/or hemicellulose) to simple sugars having from one to four saccharide units. It has been found that addition of a polysaccharide enzyme in the SSF zone advantageously provides additional fermentable sugars, which, among other benefits, results in greater ethanol yields. For example, in various embodiments, the ethanol concentration in the saccharification-fermentation mixture is at least about 0.5%, at least about 1%, at least about 2%, at least about 3%, at least about 4%, at least about 5%, at least about 6%, at least about 7%, at least about 8%, at least about 9%, or at least about 10% greater than the ethanol concentration in a fermentation mixture of the same process for producing ethanol that does not include introduction of a polysaccharide enzyme such as cellulase and/or hemicellulase into the fermentation mixture. In other embodiments, the ethanol concentration in the fermentation mixture is from about 0.5% to about 20%, from about 0.5% to about 15%, from about 0.5% to about 12%, from about 0.5% to about 10%, from about 1% to about 20%, from about 1% to about 15%, from about 1% to about 12%, from about 1% to about 10%, from about 2% to about 20%, from about 2% to about 15%, from about 2% to about 12%, from about 2% to about 10%, from about 5% to about 20%, from about 5% to about 15%, from about 5% to about 12%, from about 5% to about 10% greater than the ethanol concentration in a fermentation mixture of the same process for producing ethanol that does not include introduction of a polysaccharide enzyme such as cellulase and/or hemicellulase into the fermentation mixture.

In various embodiments, contacting the enzymatic hydrolysate in the SSF zone with the polysaccharide enzyme selected from the group consisting of cellulase, hemicellulase, and combinations thereof provides an ethanol yield increase of at least about 0.5%, at least about 1%, at least about 2%, at least about 3%, at least about 4%, at least about 5%, at least about 6%, at least about 7%, at least about 8%, at least about 9%, or at least about 10% when compared to the yield of the same process for producing ethanol that does not include introduction of a polysaccharide enzyme such as cellulase and/or hemicellulase into the fermentation mixture. In these and other embodiments, contacting the enzymatic hydrolysate in the SSF zone with the polysaccharide enzyme selected from the group consisting of cellulase, hemicellulase, and combinations thereof provides an ethanol yield increase from about 0.5% to about 20%, from about 0.5% to about 15%, from about 0.5% to about 12%, from about 0.5% to about 10%, from about 1% to about 20%, from about 1% to about 15%, from about 1% to about 12%, from about 1% to about 10%, from about 2% to about 20%, from about 2% to about 15%, from about 2% to about 12%, from about 2% to about 10%, from about 5% to about 20%, from about 5% to about 15%, from about 5% to about 12%, from about 5% to about 10% when compared to the yield of the same process for producing ethanol that does not include introduction of a polysaccharide enzyme such as cellulase and/or hemicellulase into the fermentation mixture.

Importantly, the addition of these enzymes to the SSF zone allows such embodiments of the present invention to be implemented in existing ethanol production plants with little or no modification and investment to the plant. Further, few or no operational changes to the SSF process conditions are necessary.

In various embodiments, the polysaccharide enzyme comprises a cellulase. As previously described, cellulases are a class of enzymes produced chiefly by fungi, bacteria, and protozoans that catalyze the cellulolysis (hydrolysis) of cellulose into glucose, cellobiose, cellotriose, cellotetrose, cellopentose, cellohexose, and longer chain cellodextrins. Combinations of the five basic types of cellulases may be employed. For example, endo-cellulases may be added to disrupt the crystalline structure of cellulose and expose individual cellulose chains. Exo-cellulase may be added to cleave two units (cellobiose), three units (cellotriose), or four units (cellotetrose) from the exposed chains, while beta-glucosidase may be added to hydrolyse these products into glucose, which is available for fermentation. Cellulases are commercially available from such suppliers as Novozymes and Genencor. Commercially available cellulases include GC-220 from Genencor and Cellic Ctec2 from Novozymes.

In some embodiments, the polysaccharide enzyme comprises a cellulase and a hemicellulase. Xylanases are a subset of hemicellulase enzymes which degrade the linear polysaccharide β-1,4-xylan into xylose (a monosaccharide containing five carbon atoms and including an aldehyde functional group). Hemicellulases are commercially available from such suppliers as Novozymes and Genencor.

Other enzymes may be added in the SSF zone, such as arabinoxylanases and pullulanases. Arabinoxylanases catalyze the hydrolysis of arabinoxylans, yielding arabinose and xylose. Pullulanases are a class of glucanases that catalyze the hydrolysis of amylopectin at the 1→6 bond, thereby yielding oligomers of D-glucose. A commercially available pullulanase is Promozyme® D2, available from Novozyme Corporation. Also useful are multi-enzyme complexes containing multiple carbohydrases, such as Viscozyme® L, available from Novozyme Corporation, which contains arabanase, cellulase, β-glycanase, hemicellulase, and xylanase.

The dose of polysaccharide enzyme that the enzymatic hydrolysate is contacted with may be expressed in terms of unit weight per unit weight of mash (enzymatic hydrolysate) as received. For example, the amount of polysaccharide enzyme may be at least about 0.05, at least about 0.1, at least about 0.25, or at least about 0.5 kg of polysaccharide enzyme/1000 kg of enzymatic hydrolysate (as-is). In these and other embodiments, the amount of polysaccharide enzyme is from about 0.05 to about 10, from about 0.1 to about 5, from about 0.1 to about 4 or from about 0.25 to about 4 kg of polysaccharide enzyme/1000 kg of enzymatic hydrolysate (as-is). The dose of polysaccharide enzyme that the enzymatic hydrolysate is contacted with may also be expressed in terms of unit weight per unit weight of dry feedstock. For example, the amount of polysaccharide enzyme may be at least about 0.1, at least about 0.15, at least about 0.25, at least about 0.5, or at least 1 kg of polysaccharide enzyme/1000 kg of feedstock on a dry matter basis. In various embodiments, the amount of polysaccharide enzyme is from about 0.1 to about 50, from about 0.15 to about 40, from about 0.25 to about 30 or from about 0.5 to about 25 kg of polysaccharide enzyme/1000 kg of feedstock on a dry matter basis.

Inoculation of the enzymatic hydrolysate with the yeast, the glucoamylase, and the polysaccharide enzyme may occur by continuous or batchwise addition. In various embodiments, the yeast and glucoamylase are introduced into the SSF zone simultaneously. In other embodiments, the yeast and glucoamylase are introduced into the SSF zone sequentially (e.g., less than about 1, less than about 2, less than about 3, less than about 4, or less than about 5 hours between addition of the yeast then glucoamylase or vice versa). In some embodiments, at least a portion of glucoamylase is mixed with at least a portion the enzymatic hydrolysate prior to mixing with yeast. In batch propagation or fermentation processes such prior mixing is believed to expose the yeast to a consistent initial concentration of simple sugars, neither starving the yeast with a low initial concentration nor inhibiting the yeast with a high initial concentration. In other embodiments, substantially all the glucoamylase and enzymatic hydrolysate are mixed prior to the addition of yeast. In still further embodiments, substantially all the glucoamylase and enzymatic hydrolysate are mixed immediately prior to adding such mixture to a fermentation or yeast propagation vessel containing yeast or to which yeast is concurrently or later added.

In some embodiments, the polysaccharide enzyme is introduced into the SSF zone prior to introduction of the yeast and glucoamylase into the SSF zone. In still further embodiments, the yeast, glucoamylase, and polysaccharide enzyme are introduced to the SSF zone substantially simultaneously (e.g., as a single stream or individual streams).

It is generally known that the activity of certain polysaccharide enzymes is inhibited by both glucose and ethanol. Introducing a polysaccharide enzyme in the SSF zone has been found to be beneficial not only because process modification is minimized, but also because glucose concentration is decreasing due to yeast metabolism. Even though ethanol concentration is increasing the SSF zone, it has been found that the concentration is still low enough to avoid significant inhibition of the polysaccharide enzyme activity.

In various embodiments, the polysaccharide enzyme is introduced into the SSF zone after introduction of the yeast and glucoamylase into the SSF zone (e.g., less than about 1, less than about 2, less than about 3, less than about 4, or less than about 5 hours after yeast and glucoamylase have been added). In these and other embodiments, the polysaccharide enzyme is introduced into the SSF zone after a portion of the saccharification-fermentation period has been completed. For example, the polysaccharide enzyme may be introduced into the SSF zone before less than about 10%, less than about 20%, less than about 25%, less than about 30%, less than about 40%, less than 50%, less than about 60%, less than about 70%, or less than about 75% of the saccharification-fermentation period has been completed. In these and other embodiments, the polysaccharide enzyme is introduced into the SSF zone within from about 10% to about 80%, from about 10% to about 70%, from about 10% to about 60%, from about 10% to about 50%, from about 20% to about 80%, from about 20% to about 70%, from about 20% to about 60%, from about 20% to about 50%, from about 30% to about 80%, from about 30% to about 70%, from about 30% to about 60%, from about 30% to about 50%, from about 40% to about 80%, from about 40% to about 70%, from about 40% to about 60%, from about 40% to about 50%, from about 50% to about 80%, from about 50% to about 75%, or from about 50% to about 60% of the saccharification-fermentation period.

To further enhance ethanol yield, a yeast capable of converting $C_5$ sugars to ethanol can be introduced. Accordingly, in various embodiments, the yeast comprises a $C_6$ sugar yeast and a $C_5$ sugar yeast. In some embodiments, the yeast comprises a yeast that is capable of converting $C_6$ sugars and $C_5$ sugars to ethanol.

To enhance the efficacy of saccharification and ethanol fermentation and increase the ethanol yield, additional nutrients may be added to enhance yeast proliferation, such as urea, ammonia, free-amino-nitrogen (FAN), oxygen, phosphate, sulfate, magnesium, zinc, calcium, and vitamins such as inositol, pantothenic acid, and biotin. Preferably, urea may be added to a concentration between about 0 and about 32 mmol/liter and more preferably between about 8 and about 16 mmol/liter.

Preferably, the yeast is adapted to the primary fermentation mixture prior to fermentation to ethanol by propagating yeast in at least a portion of the enzymatic hydrolysate. Propagation is typically performed by forming a propagation mixture comprising yeast, enzymatic hydrolysate, glucoamylase, and additional nutrients. In various embodiments, the propagation mixture further comprises a polysaccharide enzyme. The propagation mixture may be aerated. In aerobic conditions, the yeast preferentially converts glucose and other $C_6$ sugars to form more yeast. It is believed that such yeast progeny are more efficient at converting $C_6$ sugars to ethanol in a SSF process. For batch propagation, propagation is performed for about 15 hours once all ingredients are added to the propagation vessel, after which time the contents of the propagation vessel may be transferred to a SSF vessel. In some embodiments, a batch propagation process comprises mixing glucoamylase with at least a portion of the enzymatic hydrolysate within the glucoamylase concentration ranges described above prior to mixing with yeast to form the propagation mixture.

For continuous, batch, or fed-batch SSF, preferably a propagation mixture comprising adapted yeast is initially charged to the SSF zone. Typically, such initial charge comprises about 2% to about 5% of the initial primary SSF mixture volume. At the end of the primary SSF, the ethanol content in the beer may range from about 10 to about 15% by weight as is basis, typically from 12 to about 15% by weight as is basis, as measured by high performance liquid chromatograph (HPLC) and corrected for suspended solids in the beer.

The propagation or SSF zone 80 or both may be conducted batch-wise in stirred vessels, comprising the sequence of feeding the enzymatic hydrolysate, glucoamylase, yeast, polysaccharide enzyme and optional additional nutrients to a vessel, holding and stirring the contents of the vessel for a duration following the completion of such additions, and removing at least a portion of the contents of the vessel following the duration of stirring. Optionally, stirring may be performed during the addition step and during the removal step. In one aspect, the addition step is performed by continuously adding at least a portion of the glucoamylase and the enzymatic hydrolysate to the vessel in a substantially fixed ratio. In one aspect, at least a portion of the glucoamylase and the enzymatic hydrolysate are mixed in the substantially fixed ratio prior to being added to the vessel.

After the saccharification-fermentation period, the resulting product is a beer containing ethanol and whole stillage. The contents of the beer in approximate concentrations is as follows:

Ethanol: 10.0-15.0% by weight as-is
Total solids: 9.5-14.0% by weight as-is
Water: Balance
Distillation In various embodiments, the process of the present invention further comprises distilling the saccharification-fermentation mixture to separate at least a portion of the ethanol thereby forming: (i) a distillate product comprising ethanol and (ii) a bottoms product comprising whole stillage.

Referring again to FIG. 1, the saccharification-fermentation mixture is routed into beer still (i.e., distillation) zone 90, wherein the saccharification-fermentation mixture is distilled to carry a portion of the liquid, the high wines containing ethanol, to rectifier zone 100. The distilled high wines may then be dehydrated in dehydration zone 110 (e.g., via molecular sieve), yielding ethanol suitable for use as fuel or for consumption. The ethanol is isolated from the beer by conventional means, such as distillation, which separates the high wines (a mixture of ethanol and other liquids, such as water) from the whole stillage. Distillation generally proceeds in accordance with conventional methods known in the art using conventional apparatus as described, for example, in Distillation Technology, GEA Wiegand, 16 pages and Bioethanol Technology, GEA Wiegand, 16 pages, which are incorporated herein by reference for all relevant purposes. The material remaining in the beer still after distillation comprises whole stillage. The whole stillage passes out of the beer still at a temperature of typically about 105° C.

The process of the present invention advantageously increases ethanol yield. For example, the ethanol yield of the processes of the present invention is typically at least about 200, at least about 220, at least about 240, at least about 260, at least about 280, at least about 300, at least about 330, at least about 350, at least about 360, at least about 370, at least about 380, at least about 390, at least about 400, at least about 405, or at least about 410 liters of ethanol per metric ton of plant matter feedstock. In various embodiments, an ethanol yield of from about 200 to about 450, from about 240 to about 450, from about 280 to about 430, from about 300 to about 430, from about 330 to about 430, from about 340 to about 420, from about 350 to about 410, from about 360 to about 410, or from about 360 to about 405 liters ethanol per metric ton of plant matter feedstock is achieved.

Stillage

The processes of the present invention provide modified co-feed products having increased protein content and reduced fiber content. By converting at least a portion of complex polysaccharides of little nutritive value in the energy crop into fermentable sugars and fermenting at least a portion of the fermentable sugars to produce ethanol, the process of the present invention yields a whole stillage and feed co-product derived therefrom comprising enhanced concentrations of the components of high nutritional quality, e.g. protein and oil, and reduced concentrations of complex polysaccharides of little nutritive value, e.g., hemicellulose and cellulose.

Whole stillage may comprise between about 8% and about 20% dry matter by weight, typically between about 12% and about 14% dry matter by weight. The whole stillage typically comprises a significant residual starch fraction that was not converted to ethanol. For example, some free starch granules are not pasted and thus are not available for hydrolysis by acidic conditions or enzymatic catalysis. In some instances, starch granules are wrapped in a protein matrix and are thus not available. Enzymatic hydrolysis is not 100% efficient such that some solubilized dextrins are not hydrolyzed and are therefore not available for fermentation.

While SSF may convert between about 90% and about 97%, more typically between about 90% and about 95% of the starch portion of the grain into fermentable sugars, between about 3% and about 10%, typically about 5% and about 10% of the starch portion remains in the whole stillage. Moreover, the whole stillage comprises a significant portion of cellulose and hemicellulose. Typically, between about 12% and about 15% of the dry matter by weight in whole stillage is cellulose, while between about 17% and about 26% of the dry matter by weight in whole stillage is hemicellulose. The remainder starch, cellulose, and hemicellulose in the whole stillage may be further processed into fermentable sugars, thereby improving the overall ethanol yield of fermentation.

In accordance with the present invention, a modified feed co-product is obtained from whole stillage. In various embodiments, the modified feed co-product has a fiber (neutral detergent fiber) content of less than about 42 wt. %, less than about 40 wt. %, less than about 38 wt. %, less than about 36 wt. %, or less than about 34 wt. % on a dry matter basis. In these and other embodiments, the modified feed co-product has a fiber (neutral detergent fiber) content of from about 25 wt. % to about 45 wt. %, from about 30 wt. % to about 45 wt. %, from about 30 wt. % to about 40 wt. %, or from about 30 wt. % to about 35 wt. % on a dry matter basis.

In various embodiments, the modified feed co-product has a protein content of at least about 26 wt. %, at least about 28 wt. %, at least about 30 wt. %, at least about 32 wt. %, or at least about 34 wt. % on a dry matter basis. In these and other embodiments, the modified feed co-product has a protein content of from about 26 wt. % to about 40 wt. %, from about 28 wt. % to about 40 wt. %, from about 28 wt. % to about 34 wt. %, or from about 30 wt. % to about 34 wt. % on a dry matter basis.

The composition of the modified feed co-product may vary depending upon the plant matter feedstock used in the ethanol production process. For example, when the plant matter feedstock comprises barley, the modified feed co-product derived therefrom has a fiber content of less than about 47 wt. %, less than about 45 wt. %, or less than about 43 wt. % on a dry matter basis. In these and other embodiments, the barley based modified feed co-product has a fiber content of from about 35 wt. % to about 47 wt. %, from about 35 wt. % to about 45 wt. %, from about 35 wt. % to about 43 wt. %, or from about 40 wt. % to about 43 wt. % on a dry matter basis. In some embodiments, the barley based modified feed co-product comprises:

Protein: 28-35 wt. % dry matter basis
Fats: 2-10 wt. % dry matter basis
Fiber (neutral detergent fiber): 35-45 wt. % dry matter basis.
Ash: 2-10 wt. % dry matter basis.

In various embodiments, the plant matter feedstock comprises wheat and the modified feed co-product derived therefrom has a fiber content of less than about 42 wt. % or less than about 40 wt. %. In these and other embodiments, the wheat based modified feed co-product has a fiber content of from about 35 wt. % to about 42 wt. %, or from about 35 wt. % to about 40 wt. %. In some embodiments, the wheat based modified feed co-product comprises:

Protein: 30-35 wt. % dry matter basis
Fats: 2-10 wt. % dry matter basis
Fiber (neutral detergent fiber): 35-40 wt. % dry matter basis
Ash: 2-10 wt. % dry matter basis.

In further embodiments, the plant matter feedstock comprises corn and the modified feed co-product derived therefrom has a fiber content of less than about 38 wt. %, less than about 36 wt. %, or less than about 34 wt. %. In these and other embodiments, the corn based modified feed co-product has a fiber content of from about 30 wt. % to about 38 wt. %, from about 30 wt. % to about 36 wt. %, or from about 30 wt. % to about 34 wt. %. In some embodiments, the corn based modified feed co-product comprises:

Protein: 30-35 wt. % dry matter basis
Fats: 5-20 wt. % dry matter basis
Fiber (neutral detergent fiber): 30-36 wt. % dry matter basis
Ash: 2-10 wt. % dry matter basis.

Neutral detergent fiber (NDF) generally encompasses cellulose, lignin, and hemicellulose. The starch and sugars generally denotes fermentable sugars or sugars comprising primarily glucose polymers that may be hydrolyzed, by acid, alkaline, enzymatic, or otherwise, into fermentable sugars.

In some embodiments, the whole stillage remaining in beer still zone 90 may be further processed to convert a portion of any remaining starch, complex polysaccharides, oligosaccharides, etc. to ethanol to thereby enhance the ethanol yield of the process. Further processing removes at least a portion of the components of little nutritive value, thereby enhancing the nutritional quality of the resultant feed product by concentrating the protein and oil content. Accordingly, in some embodiments, at least a portion of the whole stillage may be subjected to additional processing as described further herein to improve alcohol yield by converting a portion of the remainder starch, cellulose, and hemicellulose into fermentable sugars for secondary fermentation. The modified feed co-product resulting therefrom, having lower fiber content and conversely a higher protein and fat content on a dry basis, is a nutritionally enhanced feed co-product. It should be noted, in this regard, that further processing may be carried out, for example on a whole stillage co-product obtained after ethanol distillation, and may also be carried out, for example, on subsequent process streams such as a WDG obtained from the centrifugation of the whole stillage or even on other co-products such as thin stillage, DDG, DDGS, and WDGS. Thus, a variety of feed co-product streams resulting from primary ethanol fermentation/distillation may be subjected to the process of the present invention.

In various embodiments, further processing of whole stillage comprises recycling at least a portion of the whole stillage back into the primary fermentation process by combining at least a portion of whole stillage with a dry milled or wet milled plant feedstock to form a liquid mash, which is then subjected to the primary ethanol fermentation process as described above, including acid hydrolysis, liquefaction, optionally primary pre-conversion, primary saccharification and ethanol fermentation. In some embodiments, between about 10% and about 40%, such as about 10% to about 30% or about 20% to about 40% of the whole stillage is recycled. In some embodiments, the whole stillage is processed to separate thin stillage from the wet cake (i.e., wet distiller's grain), e.g., by centrifugation and further processed into animal feed co-products, e.g., WDG, DDG, CDS, etc. In some embodiments, whole stillage and thin stillage are recycled back into the above-described process in forming the mash in mixing zone 20.

In some embodiments, the further processing comprises separating the liquid portion of whole stillage, i.e., the thin stillage, from the wet cake, i.e., the wet distiller's grains, and recycling at least a portion of the thin stillage into the primary fermentation process by combining at least a portion the thin stillage with whole stillage and a dry milled or wet milled plant feedstock to form a liquid mash, which is then subjected to the primary ethanol fermentation process as described above, including acid hydrolysis, liquefaction, optionally primary pre-conversion, and saccharification and primary ethanol fermentation.

Thin stillage typically comprises between about 8% and about 12% dry matter. The components and relative proportions of the total solids, i.e., dry matter, in a thin stillage feed co-product are generally as follows:

Starch: 9-16% dry matter basis
Crude protein: 18-24% dry matter basis
Fat: 16-24% dry matter basis
Crude Fiber: 2-4% dry matter basis
Ash: 8-11% dry matter basis
Insoluble solids: 0.8%-4.0% dry matter basis Typically, between about 10% and about 40%, such as about 10% to about 30% or about 20% to about 40% of the thin stillage is recycled. The thin stillage may be concentrated by evaporation to yield condensed distiller's solubles, which may also be recycled to form the mash.

Secondary Fermentation

In some embodiments, a portion of the stillage, (e.g., whole stillage, thin stillage, condensates thereof, DDG, DDGS, WDG, and WDGS) is subjected to a secondary fermentation process. The process comprises forming an acidic aqueous medium comprising the stillage or derivative thereof and having a pH from about 2 to about 6, wherein the stillage or derivative thereof comprises starch and another polysaccharide selected from the group consisting of hemicellulose and cellulose and hydrolyzing at least a portion of the starch, the another polysaccharide, or both in the acidic aqueous medium a temperature of at least about 85° C. The process also includes contacting at least a portion of the starch, the another polysaccharide, or both in the acidic aqueous medium with an enzyme selected from the group consisting of α-amylase, cellulase, hemicellulase, and combinations thereof, the enzyme catalyzing enzymatic hydrolysis of at least a portion of the starch, the another polysaccharide, or both into a fermentable sugar. Further, the process comprises contacting the fermentable sugars with a yeast. During a fermentation period at least a portion of the simple sugars derived from the starch and/or the another polysaccharide are converted by fermentation to produce ethanol. The fermentation mixture is then distilled to separate at least a portion of the ethanol thereby forming: (i) a secondary distillate product comprising ethanol; and (ii) a secondary bottoms product comprising a secondary stillage.

Referring back to FIG. 1, a portion of stillage, (e.g., whole stillage, thin stillage, condensates thereof, DDG, DDGS, WDG, and WDGS) may be subjected to thermochemical treatment zone 120 and then heating the feed co-product to thereby promote acid hydrolysis zone 130 and gelatinization of any remaining starch, complex polysaccharides, oligosaccharides, etc. to simpler carbohydrates.

In these zones, the pH of stillage is adjusted to between about 2 and about 6, such as between about 2.5 and about 5.0, preferably between about 2.5 and about 4.5, preferably about 4.5. Sulfuric acid and hydrochloric acid are typically used. For alkaline pH adjustment, ammonia is generally used. The aqueous content may also be adjusted by, for example, adding water or by condensing the process stream, to yield a composition having between about 5% dry matter by weight and about 14% dry matter by weight. The aqueous material is typically agitated, such as by paddle stirring, stir plate, vortex, or shaker.

The whole stillage is heated to a temperature between about 85° C. and about 200° C., preferably between about 85° C. and about 150° C., such as between about 135° C. and about 145° C., and, in some embodiments, at about 143° C. The whole stillage may be held at this temperature for between about 5 minutes and about 20 minutes, preferably about 10 minutes.

Thermochemical pre-treatment under acidic conditions herein pastes any remaining starch and may achieve a dextrose equivalence (DE) in the range of about 1 to about 4, such as about 1 to about 2, yielding low molecular weight carbohydrate products, including low molecular weight oligomers, trisaccharides, disaccharides, and monosaccharide C6 and C5 sugars, and renders them available for enzymate hydrolysis.

Prior to inoculation of the thermo-chemically treated mixture, the mixture is cooled in cooling zone 140 to a temperature between about 70° C. and about 90° C., preferably about 85° C. The mixture may optionally be flashed cooled to the desired temperature. If necessary, the pH of the mixture is adjusted to between about 4 and about 6.5, preferably between about 4.5 and about 6.5, more preferably between about 5 and about 6.5, such as about 5.8.

After cooling, the acid hydrolyzed feed co-product is combined with a pre-conversion enzyme, selected from a variety of enzymes, including but not limited to amylase, xylanase, cellulase, hemicellulase, and combinations of enzymes are possible for secondary pre-conversion zone 150, wherein the enzyme catalyzes enzymatic hydrolysis of at least a portion of any remaining complex polysaccharides into simple sugars, such as oligomers, C5 and C6 sugars, disaccharides, trisaccharides, etc.

The hydrolyzed mixture is then subjected to secondary pre-conversion by adding α-amylase, and, optionally other degradative enzymes to form a secondary enzymatic hydrolysate. The thermochemically treated stillage may be inoculated with one or more of the above-described enzymes to a concentration between about 0.001% and about 0.05% based on the dry weight of the solids. Inoculation may occur by continuous or batchwise addition. To enhance secondary pre-conversion, nutrients may be added, particularly a source of nitrogen such as urea or ammonia.

Secondary pre-conversion may occur for between about one and about six hours, preferably between about one and about four hours, more preferably between about two hours and about three hours, such as about three hours. Typically, the secondary pre-conversion may achieve dextrose equivalence (DE) in the range of about 10 to about 40, such as about 10 to about 30.

To prepare the secondary enzymatic hydrolysate for secondary ethanol fermentation, the temperature of the secondary enzymatic hydrolysate may be adjusted to between about 25° C. and about 35° C., preferably about 32° C. Moreover, the pH is preferably adjusted to between about 4.2 and about 4.8, preferably about 4.5.

The secondary enzymatic hydrolysate formed thereby is then cooled in cooling zone 160 and combined with glucoamylase and yeast to form a secondary fermentation medium in fermentation zone 170, whereby any fermentable sugars produced by acid hydrolysis and secondary pre-conversion are converted by secondary fermentation into ethanol. A propagation mixture comprising at least a portion of the yeast, and glucoamylase may be added to the secondary enzymatic hydrolysate. Such propagation mixture may optionally be formed from a portion of the cooled liquefied medium or from a portion of the secondary enzymatic hydrolysate. In other embodiments, the secondary fermentation mixture is formed by continuously adding at least a portion of the glucoamylase and the cooled liquefied medium. Fermentation and propagation process conditions are generally as described above with respect to fermentation zone 80.

The secondary fermentation medium is subjected to solid-liquid separation in centrifuge or filter zone 180. The liquid portion is routed to a beer still 190, wherein ethanol is isolated from the secondary beer by conventional means, such as distillation, which separates the high wines (a mixture of ethanol and other liquids, such as water) from the fermented stillage. The high wines are rectified according to conventional methods and dehydrated to produce anhydrous ethanol for use as fuel or potable ethanol. The remaining liquid portion is then condensed by evaporation and dried, yielding dry condensed solubles. The solid portion, i.e., the wet distiller's grains, may optionally be dried in drying zone 200 into dried distiller's grains and combined with the dry condensed solubles, yielding dry distiller's grains with solubles. The solids portion, (i.e., WDG) may also be dried in a drying zone 210 to produce a nutritionally enhanced DDG. The DDG and condensed solubles may be combined forming a nutritionally enhanced DDGS feed co-product.

In some embodiments, the feed co-product produced by the method of the present invention may be exposed to one or more cellulolytic micro-organism(s) capable of utilizing the fiber component of the feed co-product as a substrate for growth and proliferation, as described in PCT Publication No. WO 2009/079183 (U.S. Prov. App. Ser. No. 61/013,695; U.S. application Ser. No. 12/747,992), the entire disclosure of which is hereby incorporated as if set forth in its entirety. As therein described, cellulolytic micro-organisms are microbes possessing an enzyme or enzyme system that can break down the cellulose and/or hemicellulose to form simple sugar(s), i.e., capable of producing one or more cellulase, hemicellulase, or cellusome complex. The microbe then uses the simple sugar along with other nutrients such as nitrogen and/or phosphorous to grow and proliferate, thereby increasing the microbial protein content of the feed co-product.

Having described the invention in detail, it will be apparent that modifications and variations are possible without departing from the scope of the invention defined in the appended claims.

EXAMPLES

The following non-limiting examples are provided to further illustrate the present invention.

Example 1

In this Example, a process according to the present invention was carried out in which polysaccharide enzymes (e.g., cellulases) were added directly to the fermentor after introduction of yeast. The process of this Example is as follows:

Barley, wheat, and corn mash (feedstocks post liquefaction) were obtained from a commercial facility. The feedstock particle sizes were approximately 4 mm for barley, 4 mm for wheat, and 5 mm for corn. The mash samples had a moisture content of approximately 68 wt. %.

Yeast (Ethanol Red available from Lessafre) at a dose of 0.6 kg/kg dry grain and glucoamylase (Distillase available from Genencor) were combined with the mash samples in fermentation vessels. The vessels were maintained at approximately 32° C. The pH was adjusted to approximately 4.5 if necessary. Fifteen hours after yeast introduction, cellulase (Cellic Ctec2 available from Novozymes or equivalent) was introduced to the vessels, with the exception of the vessels containing the control samples, in the doses indicated in Tables 1-3. Saccharification and fermentation conditions were maintained for at least 72 hours. Ethanol concentration and yield increase relative to control were determined at various times during the fermentation period. Yield increase was based on the percent increase in ethanol concentration versus control ethanol concentration.

TABLE 1

Effect on ethanol yield using cellulase enzymes during fermentation of a barley feedstock

| Cellulase Dose (g cellulase/ 1000 g grain mash) | Ethanol Concentration 24 Hours After Yeast Addition (wt. %) | Ethanol Concentration 48 Hours After Yeast Addition (wt. %) | Ethanol Concentration 72 Hours After Yeast Addition (wt. %) | Yield Increase (relative to control at 72 hours) |
|---|---|---|---|---|
| 0 (control) | 9.1% | 9.0% | 9.8% | — |
| 0.25 | 9.2% | 9.9% | 10.6% | 9.0% |
| 0.5 | 9.4% | 10.3% | 10.6% | 8.8% |
| 1 | 10.1% | 10.4% | 10.7% | 10.0% |
| 0 (control) | 9.3% | 9.6% | 9.7% | — |
| 0.05 | 9.4% | 9.9% | 10.1% | 3.7% |
| 0.1 | 9.4% | 10.0% | 10.3% | 6.2% |
| 0.2 | 9.2% | 10.5% | 10.6% | 8.6% |
| 0.5 | 9.7% | 10.7% | 10.7% | 10.4% |

TABLE 2

Effect on ethanol yield using cellulase enzymes during fermentation of a wheat feedstock

| Cellulase Dose (g cellulase/ 1000 g grain mash) | Ethanol Concentration 24 Hours After Yeast Addition (wt. %) | Ethanol Concentration 72 Hours After Yeast Addition (wt. %) | Yield Increase (relative to control at 72 hours) |
|---|---|---|---|
| 0 (control) | 9.6% | 10.1% | — |
| 0.1 | 9.6% | 10.3% | 1.8% |
| 0.2 | 9.7% | 10.3% | 1.7% |
| 0.5 | 9.5% | 10.4% | 2.6% |
| 1 | 9.9% | 10.6% | 4.2% |
| 2 | 10.0% | 10.7% | 5.1% |
| 4 | 10.2% | 10.6% | 4.7% |

TABLE 3

Effect on ethanol yield using cellulase enzymes during fermentation of a corn feedstock

| Cellulase Dose (g cellulase/ 1000 g grain mash) | Ethanol Concentration 72 Hours After Yeast Addition (wt. %) | Yield Increase (relative to control at 72 hours) | Ethanol Concentration 87 Hours After Yeast Addition (wt. %) | Yield Increase (relative to control at 87 hours) |
|---|---|---|---|---|
| 0 (control) | 12.01% | — | 12.03% | — |
| 1 | 12.25% | 2.0% | 12.27% | 2.0% |
| 2 | 12.37% | 3.0% | 12.21% | 1.5% |
| 4 | 12.37% | 3.0% | 12.33% | 2.5% |

Example 2

In this Example, a process according to the present invention was carried out in which polysaccharide enzymes (e.g., cellulases) were added to a demonstration-scale vessel using barley as the feedstock. The process of this Example is as follows:

The vessel was a 75,000 L vessel. The vessel was filled with a mixture of 51,000 L of water and 24,000 kg of barley which was milled, cooked, and liquefied prior to adding to the vessel. Yeast and glucoamylase were added to the propagation tank. Cellulase was also introduced to the vessel. The mixture inside the vessel was maintained at a temperature of 32° C. and a pH of 5.2. Ethanol concentration and yield increase relative to control were determined at various times during the fermentation period, which ceased after 65 hours. Yield increase was based on the percent increase in ethanol concentration versus control ethanol concentration.

TABLE 4

Effect on ethanol yield using cellulase enzymes during fermentation of a barley feedstock

| Cellulase Dose (kg enzyme/ 1000 kg grain mash) | Ethanol Concentration 60 Hours After Yeast Addition (wt. %) | Ethanol Concentration 72 Hours After Yeast Addition (wt. %) | Yield Increase (relative to control at 72 hours) |
|---|---|---|---|
| 0 (control) | 9.8% | 9.8% | — |
| 1 | 10.9% | 10.9% | 11.2% |
| 4 | 11.2% | 11.2% | 14.3% |

Example 3

Control Experiment

A control experiment, designated Run #4139, was carried out in which glucoamylase was added in a batch, and the urea was added in two batches. The experimental conditions are as follows:

Corn flour (979 pound/hour; 444 kg/hour) was conveyed into the Mix Tank (1500 gallon capacity; 5678 Liter capacity). The flour was made by grinding #2 yellow dent corn in a Bliss Model EX 1912 TF hammer mill using 0.125 inch (3.175 mm) (38% open area) opening screens. Process water (1440 pound/hour; 653 kg/hour) was added along with thin stillage (197 pound/hour; 89.4 kg/hour) obtained from the adjacent commercial facility as back set. About 12% of the water added was backset. The thin stillage added contained 9.3% total solids by weight and 2.5% insoluble solids by weight on an as-is basis. No whole stillage was added. Mix Tank residence time was 2.7 hours, the temperature was 141° F. (60.6° C.), and the pH was maintained at 4.8 without adjustment. 96% of the total solids on a dry solids basis were provided by the corn flour in the slurry going to the jet heater.

The slurry from the Mix Tank was pumped at a rate of 2771 pounds/hour (1256.9 kg/hour) to the Model M106AS HydroHeater steam-injection jet heater. A minimum flow of 362 pounds/hour (164 kg/hour) of 150 psig (1034 kPa) saturated steam was estimated to have been delivered to the HydroHeater to give a 298° F. (147.8° C.) jet exit temperature to paste the starch. Pressures in the hold coil downstream of the jet were 51 psig (351.6 kPa) at the inlet and 45 psig (310 kPa) at the exit. The flow residence time in the cook tube was about 10 minutes.

The hot mash was flash cooled after it exited the back pressure valve from the hold coil and entered the 300 gallon (1135.6 Liter) vacuum Flash Tank. Ammonium hydroxide (26 Baume) was added to keep the pH at 5.6 and the temperature was maintained at 190° F. (87.8° C.) by vacuum cooling. α-amylase (7.6 mL/min, Novozyme Liquozyme) was added at a 0.0014 wt. enzyme/wt of dry solids dosage.

The enzyme-treated mash was then pumped to the 1100 gallon (4164 Liter) Liquefaction Tank for 100 minutes of nominal hold time at 175° F. (79.4° C.) to further liquefy the pasted starch. The pH averaged about 5.0 in the Liquefaction Hold Tank.

The pH was adjusted to 4.7 after leaving the Liquefaction Tank and the temperature was lowered to 88° F. (31° C.) using plate and frame in-line coolers. Glucoamylase was not added continuously in this trial after the coolers. The total solids were checked and inputs at the Mix tank adjusted to maintain 34% total solids as-is basis going to the Fermentors and Propagation.

The 300 gallon (1135.6 Liter) Propagation Tank was filled to the 250 gallon mark (946.4 Liter) with the cooled mash. The Propagation Tank batch was treated with glucoamylase enzyme (0.625 gallons; 2.366 Liters; Novozyme Spirizyme Fuel) for a 0.00079 pound (0.358 grams) glucoamylase enzyme per pound (0.453 kg) dry solids dosage. Lactrol antibiotic (0.01 pound; 4.54 grams) was added plus Red Star yeast (1 pound; 453.6 grams) per Propagation tank. The Propagation tank was aerated with air (100 standard cubic feet per minute; 2.83 cubic meters per minute). The Propagation tank was pitched to the Fermentor at the 5% Fermentor fill level. Each Propagation Tank took about 50 minutes to fill and was pitched to the following Fermentor after 15 hours of fermentation time.

Four Fermentors (8000 gallon capacity; 30,283 Liters) were filled for 15 hours each. Urea solution (five gallons (18.9 Liters) at a concentration of 32% solids) were added to each fermentor at the 5% fill mark and another 6.3 gallons (23.8 Liters) at the 60% fill mark. Lactrol antibiotic (0.31 pound; 0.14 kg) was added to each fermentor. The fermentation temperature was maintained at 90° F. (32° C.) by cooling jackets with temperature control and the fermentors agitation was maintained. The fermentors were dropped to the beer well after 60 hours of fermentation and the amount of beer determined by totalizing the flows which yielded 38,700 pounds (17554 kg) to 41,800 pounds (18960 kg) of beer.

Each fermentor was analyzed and the empirical data of this Example is presented in the Tables below.

Example 4

Control Experiment

A control experiment, designated Run #4146, was carried out in which glucoamylase was added in a single batch, and urea was added in a single batch. The experimental conditions are as follows:

Corn flour (1202 pounds/hour; 545 kg/hour) was conveyed into the Mix Tank (1500 gallon capacity; 5678 Liter capacity). The flour was made by grinding #2 yellow dent corn in a Bliss Model EX 1912 TF hammer mill using 0.25 inch (6.35 mm) (40% open area) opening screens. Process water (1344 pound/hour; 609 kg/hour) was added along with thin stillage (259 pounds/hour; 117.5 kg/hour) obtained from the adjacent commercial facility as back set. About 16% of the liquid added was backset. The thin stillage added contained 9.6% total solids and 1.5% insoluble solids by weight on an as-is basis. No whole stillage was added. Mix Tank residence time was 2.6 hours, the temperature was 142° F. (61.1° C.), and the pH was maintained at 4.8 without adjustment. 95.5% of the total solids on a dry solids basis were provided by the corn flour in the slurry going to the jet heater.

The slurry from the Mix Tank was pumped at a rate of 2799 pounds/hour (1269.6 kg/hour) to the Model M106AS HydroHeater steam-injection jet heater. A minimum flow of 348 pounds/hour (157.85 kg/hour) of 150 psig (1034 kPa) saturated steam was estimated to have been delivered to the HydroHeater to give a 291° F. (144° C.) jet exit temperature to paste the starch. The mean hold coil temperature was 284° F. (140° C.) in the hold coil downstream of the jet. Pressures were 58.9 psig (406 kPa) at the inlet and 49.9 psig (344 kPa) at the exit. The flow residence time in the cook tube was about 10 minutes.

The hot mash was flash cooled after it exited the back pressure valve from the hold coil and entered the 300 gallon (1135.6 Liter) vacuum Flash Tank. Ammonium hydroxide (26 Baume) was added to keep the pH at 5.75 and the temperature was maintained at 190° F. (87.8° C.) by vacuum cooling. α-amylase (5.3 mL/min; Novozyme Liquozyme) was added at a 0.00081 wt. enzyme/wt of dry solids dosage.

The enzyme-treated mash was then pumped at 6.0 gallons per minute (22.7 Liters per minute) to the 1100 gallon (4164 Liter) Liquefaction Tank for 89 minutes of nominal hold time at 188° F. (86.7° C.) to further liquefy the pasted starch. The pH averaged about 6.0 in the Liquefaction Hold Tank.

The pH was adjusted to 3.5 after leaving the Liquefaction Tank and the temperature was lowered to 88° F. (31° C.) using plate and frame in-line coolers. The total solids were checked and inputs at the Mix tank adjusted to maintain 31.7% total solids as-is basis going to the Fermentors and Propagation.

The 300 gallon (1135.6 Liter) Propagation Tank was filled to the 245 gallon (927 Liter) mark with the cooled mash. Lactrol antibiotic (0.01 pound; 4.54 grams) was added plus Red Star yeast (1 pound; 453.6 grams) per Propagation tank. The Propagation tank was aerated with air (100 standard cubic feet per minute; 2.83 cubic meters per minute). The Propagation tank was pitched to the Fermentor at the 5% Fermentor fill level. Each Propagation Tank took about 45 minutes to fill and was pitched to the following Fermentor after 15 hours of fermentation time.

Four Fermentors (8000 gallon capacity; 30,283 Liters) were filled for 15 hours each. Urea solution (10.53 gallons (39.9 Liters) of 32% solids concentration) was added to each fermentor at the 5% fill mark. Glucoamylase (4901 mL; Novozyme Spirizyme Fuel) enzyme was added to each fermentor at this time as well for a 0.00074 wt. enz./wt. of dry solids dosage. No antibiotic was added to the fermentors. The fermentation temperature was maintained at 88° F. (31° C.) by cooling jackets with temperature control and the fermentors agitation was maintained. The fermentors were dropped to the beer well after 60 hours of fermentation and the amount of beer determined by totalizing the flows which yielded 45,574 pounds (20,672 kg) to 46,881 pounds (21,265 kg) of beer.

Each fermentor was analyzed and the empirical data of this Example is presented in the Tables below.

Example 5

Control Experiment

A control experiment, designated Run #4150, was carried out in which glucoamylase was added continuously. The experimental conditions are as follows:

Corn flour (1060 pounds/hours; 480.8 kg/hour) was conveyed into the Mix Tank (1500 gallon capacity; 5678 Liter capacity). The flour was made by grinding #2 yellow dent corn in a Bliss Model EX 1912 TF hammer mill using 0.25 inch (6.35 mm) (40% open area) opening screens. Process water (1218 pound/hour; 552.5 kg/hour) was added along with thin stillage (257 pounds/hour; 116.6 kg/hour) obtained from the adjacent commercial facility as back set. About 17% of the liquid added was backset. The thin stillage added contained 9.0% total solids and 2.4% insoluble solids by weight on an as-is basis. No whole stillage was added. Mix Tank residence time was 2.5 hours, the temperature was 142° F. (61.1° C.), and the pH was maintained at 5.0 without adjustment. 91.9% of the total solids on a dry solids basis were provided by the corn flour in the slurry going to the jet heater.

The slurry from the Mix Tank was pumped at a rate of 2888 pounds/hour (1310 kg/hour) to the Model M106AS HydroHeater steam-injection jet heater. A minimum flow of 351 pounds/hour (159 kg/hour) of 150 psig (1034 kPa) saturated steam was estimated to have been delivered to the HydroHeater to give a 289° F. (142.8° C.) jet exit temperature to paste the starch. The hold coil exit temperature was not measured in the hold coil downstream of the jet. Pressures were 58.0 psig (400 kPa) at the inlet and 49.0 psig (337.8 kPa) at the exit of the hold coil. The flow residence time in the cook tube was about 10 minutes.

The hot mash was flash cooled after it exited the back pressure valve from the hold coil and entered the 300 gallon (1135.6 Liter) vacuum Flash Tank. The residence time was about 13 minutes. Ammonium hydroxide (26 Baume) was added to keep the pH at 6.2 and the temperature was maintained at 174° F. (78.9° C.) by vacuum cooling. α-amylase (5.0 mL/min, Novozyme Liquozyme) was added at a 0.00077 wt. enzyme/wt of dry solids dosage.

The enzyme-treated mash was then pumped at 6.1 gallons per minute (23.1 Liters per minute) to the 1100 gallon (4164 Liter) Liquefaction Tank for 87 minutes of nominal hold time at 132° F. (55.6° C.) to further liquefy the pasted starch. The pH averaged about 6.2 in the Liquefaction Hold Tank.

The pH was adjusted to 4.8 after leaving the Liquefaction Tank and the temperature was lowered to 88° F. (31.1° C.) using plate and frame in-line coolers. The total solids were checked and inputs at the Mix tank adjusted to maintain 31.4% total solids as-is basis going to the Fermentors and Propagation. Glucoamylase (5 mL/min.; Novozyme Spirizyme Fuel) enzyme was added continuously to the mash going to Propagation and Fermentation at this time for a 0.00073 wt. enz./wt. of dry solids dosage.

The 300 gallon (1135.6 Liter) Propagation Tank was filled to the 245 gallon (927 Liter) mark with the cooled mash. Lactrol antibiotic (0.01 pound; 4.54 grams) was added plus Red Star yeast (1 pound; 453.6 grams) per Propagation tank. The Propagation tank was aerated with air (100 standard cubic feet per minute; 2.83 cubic meters per minute). The Propagation tank was pitched to the Fermentor at the 5% Fermentor fill level. Each Propagation Tank took about 45 minutes to fill and was pitched to the following Fermentor after 15 hours of fermentation time.

Four Fermentors (8000 gallon capacity; 30,283 Liters) were filled for 15 hours each. Urea solution (11 gallons (41.6 Liters) of 32% solids concentration) was added to each fermentor at the 5% fill mark. No antibiotic was added to the fermentors. The fermentation temperature was maintained at 88° F. (31.1° C.) by cooling jackets with temperature control and the fermentors were agitated. The fermentors were dropped to the beer well after 60 hours of fermentation. The amount of beer determined by summing the flow which yielded a range of 52,832 pounds (23,964 kg) to 54,007 pounds (24,497 kg) of beer for the four fermentors.

Each fermentor was analyzed and the empirical data of this Example is presented in the Tables below.

Example 6

Whole Stillage Recycle

A process, designated Run #4209, according to the present invention was carried out in which the mash was prepared with 23% Whole Stillage recycle. The process of this Example is as follows:

Corn flour (1172 pounds/hour; 531.6 kg/hour) was conveyed into the Mix Tank (1500 gallon capacity; 5678 Liter capacity). The flour was made by grinding #2 yellow dent corn in a Bliss Model EX 1912 TF hammer mill using 0.25 inch (6.35 mm) (40% open area) opening screens. Process water (1535 pound/hour; 696.3 kg/hour) was added along with whole stillage (449 pounds/hour; 203.7 kg/hour) obtained from the adjacent commercial facility as back set. About 23% of the liquid added was whole stillage backset. The whole stillage used had 16.2% as-is basis total solids and 11.9% as-is insoluble solids. No thin stillage was added. Mix Tank residence time was 2.6 hours, the temperature was 146° F. (63.3° C.), and the pH was maintained at 5.0 without adjustment.

The slurry from the Mix Tank was pumped at a rate of 2918 pounds/hour (1323.6 kg/hour) to the Model M106AS HydroHeater steam-injection jet heater. A minimum flow of 410 pounds/hour (186 kg/hour) of 150 psig (1034 kPa) saturated steam was estimated to have been delivered to the HydroHeater to give a 300° F. (148.9° C.) jet exit temperature to paste the starch. The hold coil exit temperature was measured at 291° F. (143.9° C.) downstream of the jet. Pressures were 75.5 psig (520.5 kPa) at the inlet and 60.4 psig (416.4 kPa) at the exit of the hold coil. The flow residence time in the cook tube was about 10 minutes.

The hot mash was flash cooled after it exited the back pressure valve from the hold coil and entered the 300 gallon (1135.6 Liter) vacuum Flash Tank. The residence time was about 18 minutes. Ammonium hydroxide (26 Baume) was added to keep the pH at 6.2 and the temperature was maintained at 187° F. (86.1° C.) by vacuum cooling. α-amylase (5.0 mL/min; Novozyme Liquozyme) was added at a 0.00071 wt. enzyme/wt of dry solids dosage.

The enzyme-treated mash was then pumped at 6.0 gallons per minute (22.7 Liters per minute) to the 1100 gallon (4164 Liter) Liquefaction Tank for 89 minutes of nominal hold time at 155° F. (68.3° C.) to further liquefy the pasted starch.

The pH was adjusted to 5.0 using sulfuric acid after leaving the Liquefaction Tank and the temperature was lowered to 89° F. (31.7° C.) using plate and frame in-line coolers. Glucoamylase enzyme (6 mL/min.; Novozyme Spirizyme Fuel) was added continuously to the mash going to Propagation and Fermentation at this time for a 0.00080 wt. enz./wt. of dry solids dosage. The total solids were checked and inputs at the Mix tank adjusted to maintain 33.4% total solids as-is basis going to the Fermentors and Propagation.

The 300 gallon (1135.6 Liter) Propagation Tank was filled to the 245 gallon (927.4 Liter) mark with the cooled mash. Lactrol antibiotic (0.01 pound; 4.54 grams) was added plus Red Star yeast (1 pound; 453.6 grams) per Propagation tank. The Propagation tank was aerated with air (100 standard cubic feet per minute; 2.83 cubic meters per minute). The Propagation tank was pitched to the Fermentor at the 5% Fermentor fill level. Each Propagation Tank took about 45 minutes to fill and was pitched to the following Fermentor after 15 hours of fermentation time. Yeast counts in the Propagation Tank at transfer were: 373 million live, 145 million budding; 46 million dead.

Two 8000 gallon (30,283 Liter) Fermentors were filled for 15 hours each. Urea solution (32% solids; 11 gallons (41.6 Liters)) was added to each fermentor at the 5% fill mark. No antibiotic was added to the fermentors. The fermentation temperature was maintained at 88.5° F. (31.4° C.) by cooling jackets with temperature control and the fermentors were agitated. The fermentors were dropped to the beer well after 60 hours of fermentation and the amount of beer determined by totalizing the flow which yielded a range of 46,315 pounds (21,008 kg) to 47,566 pounds (21,576 kg) of beer for the two fermentors.

Each fermentor was analyzed and the empirical data of this Example is presented in the Tables below.

Example 7

Whole Stillage Recycle

A process, designated Run #4211, according to the present invention was carried out in which the mash was prepared with 45% Whole Stillage. The process of this Example is as follows:

Corn flour (1078 pounds/hour; 488.97 kg/hour) was conveyed into the Mix Tank (1500 gallon capacity; 5678 Liter capacity). The flour was made by grinding #2 yellow dent corn in a Bliss Model EX 1912 TF hammer mill using 0.25 inch (6.35 mm) (40% open area) opening screens. Process water (1309 pound/hour; 593.8 kg/hour) was added along with whole stillage (1062 pounds/hour; 481.7 kg/hour) obtained from the adjacent commercial facility as back set. About 45% of the liquid added was whole stillage backset. The whole stillage used had 16.4% as-is basis total solids and 10.7% as-is insoluble solids. No thin stillage was added. Mix Tank residence time was 2.6 hours, the temperature was 141° F. (60.6° C.), and the pH was maintained at 5.1 without adjustment. 82.8% of the dry solids were estimated to be provided by the corn flour.

The slurry from the Mix Tank was pumped at a rate of 2924 pounds/hour (1326 kg/hour) to the Model M106AS HydroHeater steam-injection jet heater. A steam flow of 468 pounds/hour (212.3 kg/hour) of 150 psig (1034 kPa) saturated steam was measured to the HydroHeater to give a 297° F. (147.2° C.) jet exit temperature to paste the starch. The hold coil exit temperature was measured at 291° F. (143.9° C.) downstream of the jet. Pressures were 72.6 psig (500.6 kPa) at the inlet and 56.5 psig (389.6 kPa) at the exit of the hold coil. The flow residence time in the cook tube was about 10 minutes.

The hot mash was flash cooled after it exited the back pressure valve from the hold coil and entered the 300 gallon (1135.6 Liter) vacuum Flash Tank. The tank residence time was about 20 minutes. Ammonium hydroxide (26 Baume) was added to keep the pH at 6.2 and the temperature was maintained at 188° F. (86.7° C.) by vacuum cooling. α-amylase (5.5 mL/min; Novozyme Liquozyme) was added at a 0.00085 wt. enzyme/wt of dry solids dosage.

The enzyme-treated mash was then pumped at 5.6 gallons per minute (21.2 Liters per minute) to the 1100 gallon (4164 Liter) Liquefaction Tank for 88 minutes of nominal hold time at 168° F. (75.6° C.) to further liquefy the pasted starch.

The pH was adjusted to 4.4 using sulfuric acid after leaving the Liquefaction Tank and the temperature was lowered to 88° F. (31.1° C.) using plate and frame in-line coolers. Glucoamylase enzyme (6.8 mL/min.; Novozyme Spirizyme Fuel) enzyme was added continuously to the mash going to Propagation and Fermentation at this time for a 0.00099 wt. enz./wt. of dry solids dosage. The total solids were checked and inputs at the Mix tank adjusted to maintain 33.2% total solids as-is basis going to the Fermentors and Propagation.

The 300 gallon (1135.6 Liter) Propagation Tank was filled to the 250 gallon (946.4 Liter) mark with the cooled mash. Lactrol antibiotic (0.01 pound; 4.54 grams) was added plus Red Star yeast (1 pound; 453.6 grams) per Propagation tank. The Propagation tank was aerated with air (100 standard cubic feet per minute; 2.83 cubic meters per minute). The Propagation tank was pitched to the Fermentor at the 5% Fermentor fill level. Each Propagation Tank took about 45 minutes to fill and was pitched to the following Fermentor after 15 hours of fermentation time. Yeast counts in the Propagation Tank at transfer were: 283 million live, 156 million budding; 28 million dead.

Two 8000 gallon (30,283 Liter) Fermentors were filled for 15 hours each. Urea solution (32% solids; 11 gallons (41.6 Liters)) was added to each fermentor at the 5% fill mark. No antibiotic was added to the fermentors. The fermentation temperature was maintained at 84.2° F. (29° C.) and 91.8° F. (33.2° C.) by cooling jackets with temperature control and the fermentors were agitated. The fermentors were dropped to the beer well after 60 hours of fermentation and the amount of beer determined by totalizing the flow which yielded a range of 44,579 pounds (20,221 kg) to 44,921 pounds (20,376 kg) of beer for the two fermentors.

Each fermentor was analyzed and the empirical data of this Example is presented in the Tables below.

Example 8

Fine Milling of Corn

A process, designated Run #4255, according to the present invention was carried out in which the mash was prepared with finely milled corn. The process of this Example is as follows:

Corn flour (1188 pounds/hour; 538.9 kg/hour) was conveyed into the Mix Tank (1500 gallon capacity; 5678 Liter capacity). The flour was made by grinding #2 yellow dent corn in a Bliss Model EX 1912 TF hammer mill using 0.125 inch (3.175 mm) (38% open area) opening screens. Process water (1747 pound/hour; 792.4 kg/hour) was added along with thin stillage (349 pounds/hour; 158.3 kg/hour) obtained from the adjacent commercial facility as back set. About 16.6% of the liquid added was thin stillage backset. The thin stillage used had 10.3% as-is basis total solids and 3.7% as-is insoluble solids. No whole stillage was added. Mix Tank residence time was 1.9 hours, the temperature was 145° F. (62.8° C.), and the pH was maintained at 4.8 without adjustment. 95.8% of the dry solids were estimated to be provided by the corn flour.

The slurry from the Mix Tank was pumped at a rate of 3154 pounds/hour (1430.6 kg/hour) to the Model M106AS HydroHeater steam-injection jet heater. A steam flow of 545 pounds/hour (247.2 kg/hour) of 150 psig (1034 kPa) saturated steam was measured to the HydroHeater to give a 292° F. (144.4° C.) jet exit temperature to paste the starch. The hold coil exit temperature was measured at 286° F. (141.1° C.) downstream of the jet. Pressures were 80.4 psig (554.3 kPa) at the inlet and 37.2 psig (256.5 kPa) at the exit of the hold coil. The flow residence time in the cook tube was about 10 minutes.

The hot mash was flash cooled after it exited the back pressure valve from the hold coil and entered the 300 gallon (1135.6 Liter) vacuum Flash Tank. The tank residence time was about 17 minutes. Ammonium hydroxide (26 Baume) was added to keep the pH at 5.2 and the temperature was maintained at 173° F. (78.3° C.) by vacuum cooling. α-amylase (5.0 mL/min; Novozyme Liquozyme) was added at a 0.00067 wt. enzyme/wt of dry solids dosage.

The enzyme-treated mash was then pumped at 5.6 gallons per minute (21.2 Liters per minute) to the 1100 gallon (4164 Liter) Liquefaction Tank for 81 minutes of nominal hold time at 186° F. (85.6° C.) to further liquefy the pasted starch.

The pH was adjusted to 4.2 using sulfuric acid after leaving the Liquefaction Tank and the temperature was lowered to 89° F. (31.7° C.) using plate and frame in-line coolers. Glucoamylase enzyme (6.0 mL/min.; Novozyme Spirizyme Fuel) enzyme was added continuously to the mash going to Propagation and Fermentation at this time for a 0.00076 wt. enz./wt. of dry solids dosage. The total solids were checked and inputs at the Mix tank adjusted to maintain 33.6% total solids as-is basis going to the Fermentors and Propagation.

The 300 gallon (1135.6 Liter) Propagation Tank was filled to the 245 gallon (927.4 Liter) mark with the cooled mash. Lactrol antibiotic (2 grams) was added plus Red Star yeast (1 pound; 453.6 grams) per Propagation tank. The Propagation tank was aerated with air (20 standard cubic feet per minute; 0.57 cubic meters per minute). The Propagation tank was pitched to the Fermentor at the 5% Fermentor fill level. Each Propagation Tank took about 45 minutes to fill and was pitched to the following Fermentor after 15 hours of fermentation time. Yeast counts in the Propagation Tank at transfer were: 420 million live, 171 million budding; 45 million dead.

Three 8000 gallon (30,283 Liter) Fermentors were filled for 15 hours each. Urea solution (32% solids; 11 gallons (41.6 Liters)) was added to each fermentor at the 5% fill mark. No antibiotic was added to the fermentors. The fermentation temperature was maintained at 88.4° F. (31.3° C.) by cooling jackets with temperature control and the fermentors were agitated. The fermentors were dropped to the beer well after 60 hours of fermentation and the amount of beer determined by totalizing the flow which yielded a range of 50,183 pounds (22,763 kg) to 51,060 pounds (23,160 kg) of beer for the two fermentors retained in the yield analysis. The third fermentor was not included because the Propagation seed yeast counts were too low.

Two fermentors were analyzed and the empirical data of this Example is presented in the Tables below.

Example 9

Fine Milling of Corn and Whole Stillage Recycle

A process, designated Run #4278, according to the present invention was carried out in which the mash was prepared with finely milled corn. Moreover, the mash comprised 17% whole stillage recycle. The process of this Example is as follows:

Corn flour (1252 pounds/hour; 567.9 kg/hour) was conveyed into the Mix Tank (1500 gallon capacity; 5678 Liter capacity). The flour was made by grinding #2 yellow dent corn in a Bliss Model EX 1912 TF hammer mill using 0.125 inch (3.175 mm) (38% open area) opening screens. Process water (1674 pound/hour; 759.3 kg/hour) was added along with whole stillage (345 pounds/hour; 156.5 kg/hour) obtained from the adjacent commercial facility as back set. About 17% of the liquid added was whole stillage backset. The whole stillage used had 16.5% as-is basis total solids and 8.3% as-is insoluble solids. No thin stillage was added. Mix Tank residence time was 1.9 hours, the temperature was 145° F. (62.8° C.), and the pH was maintained at 5.2 without adjustment. 93.9% of the dry solids were estimated to be provided by the corn flour.

The slurry from the Mix Tank was pumped at a rate of 3143 pounds/hour (1425.6 kg/hour) to the Model M106AS HydroHeater steam-injection jet heater. A steam flow of 416 pounds/hour (188.7 kg/hour) of 150 psig (1034 kPa) saturated steam was measured to the HydroHeater to give a 296° F. (146.7° C.) jet exit temperature to paste the starch. The hold coil exit temperature was measured at 290° F. (143.3° C.) downstream of the jet. Pressures were 83.8 psig (577.8 kPa) at the inlet and 51.6 psig (355.8 kPa) at the exit of the hold coil. The flow residence time in the cook tube was about 10 minutes.

The hot mash was flash cooled after it exited the back pressure valve from the hold coil and entered the 300 gallon (1135.6 Liter) vacuum Flash Tank. The tank residence time was about 17 minutes. Ammonium hydroxide (26 Baume) was added to keep the pH at 5.9 and the temperature was maintained at 167° F. (75° C.) by vacuum cooling. α-amylase (5.0 mL/min; Novozyme Liquozyme) was added at a 0.00065 wt. enzyme/wt of dry solids dosage.

The enzyme-treated mash was then pumped at 6.5 gallons per minute (24.6 Liters per minute) to the 1100 gallon (4164 Liter) Liquefaction Tank for 90 minutes of nominal hold time at 180° F. (82.2° C.) to further liquefy the pasted starch.

The pH was adjusted to 5.0 using sulfuric acid after leaving the Liquefaction Tank and the temperature was lowered to 91° F. (32.8° C.) using plate and frame in-line coolers. Glucoamylase enzyme (6.0 mL/min.; Novozyme Spirizyme Fuel) enzyme was added continuously to the mash going to Propagation and Fermentation at this time for a 0.00074 wt. enz./wt. of dry solids dosage. The total solids were checked and inputs at the Mix tank adjusted to maintain 34.6% total solids as-is basis going to the Fermentors and Propagation.

The 300 gallon (1135.6 Liter) Propagation Tank was filled to the 245 gallon (927.4 Liter) mark with the cooled mash. Lactrol antibiotic (2 grams) was added plus Red Star yeast (1 pound; 453.6 grams) per Propagation tank. The Propagation tank was aerated with air (20 standard cubic feet per minute; 0.57 cubic meters per minute). The Propagation tank was pitched to the Fermentor at the 5% Fermentor fill level. Each Propagation Tank took about 45 minutes to fill and was pitched to the following Fermentor after 8 hours of fermentation time. Yeast counts in the two Propagation Tanks measured at transfer averaged: 385 million live, 146 million budding; 56 million dead for the two Prop Tanks analyzed for yeast counts. Propagation Tank C was not measured.

Three 8000 gallon (30,283 Liter) Fermentors were filled for 8 hours each. Urea solution (32% solids; 11 gallons (41.6 Liters)) was added to each fermentor at the 5% fill mark. No antibiotic was added to the fermentors. The fermentation temperature was maintained at 87.4° F. (30.8° C.) by cooling jackets with temperature control and the fermentors were agitated. Fermentor C was maintained at a higher temperature of 89.1° F. (31.7° C.). The fermentors were dropped to the beer well after 60 hours of fermentation and the amount of beer determined by totalizing the flow which yielded a range of 24,961 pounds (11,322 kg) to 25,569 pounds (11,598 kg) of beer for the fermentors.

Two of the fermentors had high residual starch and D-glucose in the beers and were excluded from the analysis. Fermentor A was analyzed and the empirical data of this Example is presented in the Tables below.

Example 10

Post-Liquefaction Enzymes

A process, designated Run #7008, according to the present invention was carried out in which enzymes were added post-liquefaction and prior to ethanol fermentation. The process of this Example is as follows:

Corn flour (1242 pounds/hour; 563.4 kg/hour) was conveyed into the Mix Tank (1500 gallon capacity; 5678 Liter capacity). The flour was made by grinding #2 yellow dent corn in a Bliss Model EX 1912 TF hammer mill using 0.125 inch (3.175 mm) (38% open area) opening screens. Process water (1589 pound/hour; 720.8 kg/hour) was added along with thin stillage (326 pounds/hour; 147.9 kg/hour) obtained from the adjacent commercial facility as back set. About 17% of the liquid added was thin stillage backset. The thin stillage used had a 9.30% as-is basis total solids and 1.50% as-is insoluble solids. No whole stillage was added. Mix Tank residence time was 1.8 hours, the temperature was 141° F. (60.6° C.), and the pH was maintained at 5.0 without adjustment. 96.5% of the dry solids were estimated to be provided by the corn flour to the Mix Tank.

The slurry from the Mix Tank was pumped at a rate of 3152 pounds/hour (1429.7 kg/hour) to the Model M106AS HydroHeater steam-injection jet heater. A steam flow of 404 pounds/hour (183.3 kg/hour) of 150 psig (1034 kPa) saturated steam was measured to the HydroHeater to give a 290° F. (143.3° C.) jet exit temperature to paste the starch. The hold coil exit temperature was measured at 275° F. (135° C.) downstream of the jet. Pressures were 58.6 psig (404.0 kPa) at the inlet and 46.0 psig (317.2 kPa) at the exit of the hold coil. The flow residence time in the cook tube was about 7 minutes.

The hot mash was flash cooled after it exited the back pressure valve from the hold coil and entered the 300 gallon (1135.6 Liter) vacuum Flash Tank. The tank residence time was about 25 minutes. Ammonium hydroxide (26 Baume) was added to keep the pH at 5.95 and the temperature was maintained at 187° F. (86.1° C.) by vacuum cooling. α-amylase (2.0 mL/min; Novozyme Liquozyme SC-DS) was added at a 0.00028 wt. enzyme/wt of dry solids dosage.

The enzyme-treated mash was then pumped at 5.4 gallons per minute (20.4 Liters per minute) to the 1100 gallon (4164 Liter) Liquefaction Tank for 99 minutes of nominal hold time at 182° F. (83.3° C.) to further liquefy the pasted starch. The total solids in the mash were checked and inputs at the Mix tank adjusted to maintain 34.1% total solids as-is basis going to the post-liquefaction and Propagation.

The pH was adjusted to 4.6 using sulfuric acid after leaving the Liquefaction Tank and the mash was sent to one of the 8000 gallon (30,283 Liter) Fermentors through the plate and frame heat exchanger and the temperature was lowered to 130° F. (54.4° C.). The post-liquefaction enzyme treatment was conducted in each Fermentor for the duration of the 16 hour fill time. Novozymes Viscozyme L carbohydrase (0.025%; 15 lb.); Genencor FermGen acid protease (0.001%; 0.6 lb.); and Genencor GC220 cellulase (15 lb.; 0.025%) enzymes were added to the Fermentor for the post-liquefaction treatment at the 15% tank fill (1550 gallon; 5867.4 Liter) level when the lower agitator in each Fermentor became flooded. The post-liquefaction treatment in Fermentor C was conducted at a low average temperature of 116° F. (46.7° C.) and became infected with lactic acid bacteria. For this reason it has been excluded from the analysis. No glucoamylase was added to the Fermentors until after the post-liquefaction treatment.

When the 16 hour fill was completed, the temperature in the Fermentor was reduced by applying cooling water to the tank jacket to reach 89° F. (31.7° C.) where it was maintained for the 60 hour saccharification and fermentation. The pH was adjusted to 4.5 if necessary and glucoamylase enzymes (1.27 gallons; 4.8 Liters; Novozymes Spirizyme Fuel) was added to each Fermentor for a 0.00071 wt. GA enz./wt. of dry solids dosage.

The 300 gallon (1135.6 Liter) Propagation Tank was filled to the 284 gallon (1075.1 Liter) mark with the cooled mash. Cooling water was applied to the jacket to reduce the temperature from 131° F. (55° C.) to 90° F. (32.2° C.) and the pH was adjusted to 4.5 before Lactrol antibiotic (3 g) were added plus Red Star yeast (3 pounds; 1.36 kg) per Propagation tank and glucoamylase enzyme (300 mL). The Propagation tank was aerated with air (20 standard cubic feet per minute; 0.57 cubic meters per minute). Urea solution (13 gallons; 49.2 Liters; 32% solids) was added to each Propagation Tank. Yeast growth was allowed to proceed for 12 hours before pitching the Propagation Tank to the Fermentor. 265 gallons (1003 Liters) of inoculum were pitched to the Fermentor and about 19 gallons (71.9 Liters) were lost as carbon dioxide, water vapor, and alcohol vapor from the Propagation tank prior to transfer. The Propagation tank was pitched to the Fermentor after the post-liquefaction treatment and the Fermentor pH and temperature were adjusted. Yeast counts in the two Propagation Tanks measured at transfer averaged: 647 million live, 247 million budding; 62 million dead for the two Prop Tanks analyzed for yeast counts. Propagation Tank A was not measured.

Three 8000 gallon (30,283 Liter) Fermentors were filled for 16 hours each. No urea or antibiotic was added directly to the fermentors. The fermentation temperature was maintained at 89.2° F. (31.8° C.) by cooling jackets with temperature control and the fermentors were agitated. Fermentor C was maintained at a lower temperature of 88.3° F. (31.3° C.). The two fermentors analyzed were dropped to the beer well after 60 hours of fermentation and the amount of beer determined by totalizing the flow which yielded a range of 43,770 pounds (19,854 kg) to 46,987 pounds (21,313 kg) of beer for the fermentors.

Fermentor C had high lactic acid and was excluded from the analysis. Fermentors A and D were analyzed and the empirical data of this Example is presented in the Tables below.

Example 11

Control Experiment

A control experiment, designated Run #7016, was carried out without the post-liquefaction enzymes. The experimental conditions are as follows:

Corn flour (1294 pounds/hour; 586.9 kg/hour) was conveyed into the Mix Tank (1500 gallon capacity; 5678 Liter capacity). The flour was made by grinding #2 yellow dent corn in a Bliss Model EX 1912 TF hammer mill using 0.125 inch (3.175 mm) (38% open area) opening screens. Process water (1578 pounds/hour; 715.8 kg/hour) was added with thin stillage (302 pounds/hour; 137) obtained from the adjacent commercial facility as back set. About 16.1% of the liquid added was thin stillage backset. The thin stillage used had 8.31% as-is basis total solids and 0.79% as-is insoluble solids. No whole stillage was added. Mix Tank residence time was 1.8 hours, the temperature was 139° F. (59.4° C.), and the pH was maintained at 5.0 without adjustment. 97.2% of the dry solids were estimated to be provided by the corn flour to the Mix Tank.

The slurry from the Mix Tank was pumped at a rate of 3127 pounds/hour (1418.4 kg/hour) of to the Model M106AS HydroHeater steam-injection jet heater. A steam flow of 426 pounds/hour (193.2 kg/hour) of 150 psig (1034 kPa) saturated steam was measured to the HydroHeater to give a 290° F. (143.3° C.) jet exit temperature to paste the starch. The hold coil exit temperature was measured at 280° F. (137.8° C.) downstream of the jet. Pressures were 70.3 psig (484.7 kPa) at the inlet and 47.8 psig (329.6 kPa) at the exit of the hold coil. The flow residence time in the cook tube was about 7 minutes.

The hot mash was flash cooled after it exited the back pressure valve from the hold coil and entered the 300 gallon (1135.6 Liter) vacuum Flash Tank. The tank residence time was about 25 minutes. Ammonium hydroxide (26 Baume) was added to keep the pH at 6.11 and the temperature was maintained at 185.5° F. (85.3° C.) by vacuum cooling. α-amylase (2.0 mL/min; Novozyme Liquozyme SC-DS) was added at a 0.00028 wt. enzyme/wt of dry solids dosage.

The enzyme-treated mash was then pumped at 5.34 gallons per minute (20.21 Liters per minute) to the 1100 gallon (4164 Liter) Liquefaction Tank for 87.3 minutes of nominal hold time at 181° F. (82.8° C.) to further liquefy the pasted starch.

The pH was adjusted to 4.5 using sulfuric acid after leaving the Liquefaction Tank and the temperature was lowered to 90° F. (32.2° C.) using plate and frame in-line coolers. Glucoamylase enzyme (6.0 mL/min.; Novozyme Spirizyme Fuel) enzyme was added continuously to the cooled mash going to Propagation and Fermentation at this time for a 0.00071 wt. enz./wt. of dry solids dosage. The total solids were checked and inputs at the Mix tank adjusted to maintain 34.8% total solids as-is basis going to the Fermentors and Propagation.

The 300 gallon (1135.6 Liter) Propagation Tank was filled to the 285 gallon (1078.8 Liter) mark with the cooled mash. Lactrol antibiotic (3 grams) was added plus Red Star yeast (3 pound; 1.36 kg) per Propagation tank. The Propagation tank was aerated with air (20 standard cubic feet per minute; 0.57 cubic meters per minute). The Propagation tank was pitched to the Fermentor at the 5% Fermentor fill level. 245 gallons (927.4 Liters) of inoculum were pitched to the Fermentor and about 40 gallons (151 Liters) were lost as carbon dioxide, water vapor, and alcohol vapor from the Propagation tank prior to transfer. Each Propagation Tank took about 45 minutes to fill and was pitched to the following Fermentor after 12 hours of fermentation time. Yeast counts in the Propagation Tank at transfer were: 642 million live, 334 million budding; 65 million dead.

Three 8000 gallon (30,283 Liter) Fermentors were filled for 15 hours each. Urea solution (32% solids; 13 gallons (49.2 Liters)) was added to each fermentor at the 5% fill mark. No antibiotic was added to the fermentors. The fermentation temperature was maintained at 91° F. (32.8° C.) by cooling jackets with temperature control and the fermentors were agitated. The fermentors were dropped to the beer well after 60 hours of fermentation and the amount of beer determined by totalizing the flow and/or from the volume in the tanks prior to the drop yielded a range of 44,390 pounds (20,135 kg) to 47,083 pounds (21,356 kg) of beer for the two fermentors retained in the yield analysis. The third fermentor was not included because the residual starch and sugars were very high and the alcohol low. The temperature control for the first 5 hours of fermentation was far out of range for this fermentor (D) and shock to the yeast is thought to have occurred.

Two fermentors were analyzed and the empirical data of this Example is presented in the Tables below.

TABLE 5

Flour Mean Particle Sizes

| Run | Mill Screen Size (inches/mm) | Flour mean particle size, measured internally (micrometers) | Flour mean particle size, measured by Outside Lab (micrometers)* |
|---|---|---|---|
| #4139 | 0.125 inch/3.175 mm | 808.4 | 590.1 |
| #4146 | 0.25 inch/6.35 mm | 608.3 | NM |
| #4150 | 0.25 inch/6.35 mm | 848.6 | 586.5 |
| #4209 | 0.25 inch/6.35 mm | 878.4 | 621.1 |
| #4211 | 0.25 inch/6.35 mm | 794.1 | NM |
| #4255 | 0.125 inch/3.175 mm | 1152.3 | 598.6 |
| #4278 | 0.125 inch/3.175 mm | 942.5 | NM |
| #7008 | 0.125 inch/3.175 mm | 704.5 | NM |
| #7016 | 0.125 inch/3.175 mm | 677.9 | NM |

*NM = not measured

TABLE 6

Flour Dry Solids Content

| Run | Dry solids content (wt. %), measured internally | Dry solids content (wt. %), measured by Outside Lab* |
|---|---|---|
| #4139 | 87.9 | 86.8 |
| #4146 | 91.1 | NM |
| #4150 | 87.3 | 87.4 |
| #4209 | 87.7 | 88.4 |
| #4211 | 89.9 | NM |
| #4255 | 89.6 | 87.8 |
| #4278 | 88.2 | 85.8 |
| #7008 | 85.2 | 84.8 |
| #7016 | 85.3 | 84.9 |

*NM = not measured

TABLE 7

Corn Flour Nutrition

| Run | Crude Protein, % DB | ADICP, % DB | Crude Fat, % DB | Ash, % DB |
|---|---|---|---|---|
| #4139 | 8.58 | 0.45 | 3.85 | 1.29 |
| #4146 | NM | NM | NM | NM |
| #4150 | 8.10 | 0.30 | 3.95 | 1.24 |
| #4209 | 8.59 | 0.35 | 3.95 | 1.40 |
| #4211 | NM | NM | NM | NM |
| #4255 | 8.6 | 0.5 | 3.6 | 1.2 |
| #4278 | 9.2 | 0.8 | 3.9 | 1.3 |
| #7008 | 8.3 | NM | 3.5 | 1.3 |
| #7016 | 8.7 | NM | 2.6 | 3.7 |

% DB = % Dry Basis
ADICP = Acid Detergent Insoluble Crude Protein

TABLE 8

Corn Flour Nutrition (Continued)

| Run | ADF, % DB | NDF, % DB | Crude Fiber, % DB | Starch, % DB |
|---|---|---|---|---|
| #4139 | 2.25 | 9.25 | NM | 74.59 |
| #4146 | NM | NM | NM | 74 (est.) |
| #4150 | 2.35 | 10.25 | NM | 74 (est.) |
| #4209 | 2.60 | 10.55 | NM | 74 (est.) |
| #4211 | NM | NM | NM | 74 (est.) |
| #4255 | 2.8 | 11.9 | NM | 72.1 |
| #4278 | 3.6 | 19.4 | NM | 68.2 |
| #7008 | 3.6 | 10.0 | 2.6 | 70.7 |
| #7016 | 0.7 | 3.3 | 13.8 | 71.3 |

% DB = % Dry Basis
ADF = Acid Detergent Fiber
NDF = Neutral Detergent Fiber

TABLE 9

Ethanol Content of Beer and Ethanol Yield

| Run | Mean Ethanol Content in Beer (wt. %, correct) | Content Standard Deviation | Yield, (kg ethanol per kg corn dry solids) | Yield Standard Deviation |
|---|---|---|---|---|
| #4139 | 12.66 | 0.49 | 0.347 | 0.009 |
| #4146 | 12.56 | 0.33 | 0.362 | 0.021 |
| #4150 | 12.31 | 0.42 | 0.358 | 0.012 |
| #4209 | 14.43 | 0.34 | 0.404 | 0.003 |
| #4211 | 12.61 | 0.20 | 0.398 | 0.020 |
| #4255 | 12.88 | 0.20 | 0.358 | 0.006 |
| #4278 | 13.27 | — | 0.366 | — |
| #7008 | 13.66 | 0.12 | 0.369 | 0.0006 |
| #7016 | 13.37 | 0.001 | 0.359 | 0.011 |

TABLE 10

Solids Content of Beer

| Run | Total solids, wt. % | Standard deviation of Total Solids, wt. % | Insoluble Solids, wt. % | Standard deviation of Insoluble Solids, wt. % |
|---|---|---|---|---|
| #4139 | 11.36 | 0.625 | 5.53 | 0.515 |
| #4146 | 11.81 | 2.378 | 5.25 | 1.006 |
| #4150 | 10.78 | 1.540 | 5.31 | 0.716 |
| #4209 | 10.69 | 1.049 | 4.64 | 0.031 |
| #4211 | 10.71 | 0.786 | 3.65 | 0.527 |
| #4255 | 10.14 | 2.067 | 4.12 | 1.245 |
| #4278 | 12.47 | — | 5.94 | — |
| #7008 | 12.13 | 0.558 | 5.98 | 0.100 |
| #7016 | 12.81 | 0.322 | 6.69 | 0.475 |

TABLE 11

Beer Solids Nutrition

| Run | Crude Protein, % DB | ADF, % DB | NDF, % DB | Crude Fiber, % DB |
|---|---|---|---|---|
| #4139 | 32.2 | 13.75 | 36.8 | NM |
| #4146 | NM | NM | NM | NM |
| #4150 | 30.1 | 11.9 | 34.15 | NM |
| #4209 | 31.85 | 15.75 | 36.05 | NM |
| #4211 | NM | NM | NM | NM |
| #4255 | 30.75 | 13.4 | 32.6 | NM |
| #4278 | 32.7 | 14.7 | 34 | NM |
| #7008 | 29.7 | 11.85 | 22.1 | NM |
| #7016 | 30.35 | 14.5 | 24 | 9.2 |

% DB = % Dry Basis
ADF = Acid Detergent Fiber
NDF = Neutral Detergent Fiber

TABLE 12

Beer Solids Nutrition (Continued)

| Run | Crude Fat, % DB | Ash, % DB | Starch and Sugars, % DB | Water Insoluble Starch, % DB |
|---|---|---|---|---|
| #4139 | 12.6 | 8.80 | 1.9 | NM |
| #4146 | NM | NM | NM | NM |
| #4150 | 10.55 | 9.35 | 7.42 | NM |
| #4209 | 12.5 | 11.03 | 1.02 | NM |
| #4211 | NM | NM | NM | NM |
| #4255 | 11.45 | 5.24 | 0.87 | NM |
| #4278 | 12.5 | 5.17 | 0.85 | NM |
| #7008 | 6.4 | 6.06 | 3.27 | 1.61 |
| #7016 | 11.4 | 7.00 | 5.63 | 2.92 |

% DB = % Dry Basis

Runs #4139, #4145, #4150, and #7106 are control experiments. The ethanol yields (in terms of kg ethanol per kg corn dry solids) for these experiments were 0.347, 0.362, 0.358, and 0.359, respectively. The average yield of these four runs is therefore 0.3565 kg ethanol per kg corn dry solids. Runs #4209, #4211, #4255, #4278, and #7008 are experiments based on methods of the present invention, even though the conditions were varied. The ethanol yields (in terms of kg ethanol per kg corn dry solids) for these experiments were 0.404, 0.398, 0.358, and 0.366, and 0.369 respectively. The average yield of these five runs is therefore 0.379 kg ethanol per kg corn dry solids. The ethanol yield increase for the five examples according to the present invention was therefore 6.3% higher than the four control runs. The methods of Examples 4 and 5, both of which incorporated whole stillage recycle, gave the largest increases in ethanol yield.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawing shall be interpreted as illustrative and not in a limiting sense.

What is claimed is:

1. A process for producing ethanol, the process comprising:
   forming an acidic aqueous medium comprising a plant matter feedstock and having a pH of from about 2 to about 6, wherein the plant matter comprises starch and another polysaccharide selected from the group consisting of cellulose, hemicellulose, and combinations thereof;
   hydrolyzing at least a portion of the starch, the another polysaccharide, or both in the acidic aqueous medium at a temperature of at least 85° C.;
   contacting at least a portion of the starch in the acidic aqueous medium with an α-amylase, which catalyzes enzymatic hydrolysis of at least a portion of the starch to yield an enzymatic hydrolysate containing simple sugars having from one to three saccharide units; and
   contacting the enzymatic hydrolysate in a simultaneous saccharification-fermentation (SSF) zone with a yeast, a glucoamylase, and a polysaccharide enzyme selected from the group consisting of cellulase, hemicellulase, and combinations thereof to form a saccharification-fermentation mixture, wherein the polysaccharide enzyme catalyzes the hydrolysis of at least a portion of the another polysaccharide to simple sugars having from one to four saccharide units, wherein said polysaccharide enzyme is introduced into the SSF zone after introduction of the yeast and glucoamylase into the SSF zone, wherein during a saccharification-fermentation period at least a portion of the simple sugars derived from the starch are converted by fermentation to produce ethanol within the SSF zone and at least a portion of the simple sugars derived from the another polysaccharide are converted by fermentation to produce ethanol within the SSF zone, wherein said polysaccharide enzyme is introduced at a point within from about 10% to about 80% of the duration of the saccharification-fermentation period; and
   wherein the process provides an ethanol yield increase of at least 2% as compared to the yield for a same process for producing ethanol that does not include introduction of said polysaccharide enzyme into the SSF zone.

2. The process of claim 1 further comprising:
   contacting at least a portion of the aqueous medium in a liquefaction zone with a polysaccharide enzyme selected from the group consisting of cellulase, hemicellulase, and combinations thereof, wherein the polysaccharide enzyme catalyzes the hydrolysis of at least a portion of the another polysaccharide to simple sugars having from one to four saccharide units.

3. The process of claim 1 further comprising:
   contacting the enzymatic hydrolysate with a polysaccharide enzyme selected from the group consisting of cellulase, hemicellulase, and combinations thereof and reducing the temperature of the enzymatic hydrolysate in a cooling zone, wherein the polysaccharide enzyme catalyzes the hydrolysis of at least a portion of the another polysaccharide to simple sugars having from one to four saccharide units.

4. The process of claim 1 wherein the plant matter feedstock comprises milled fruits or seeds of an energy crop.

5. The process of claim 4 wherein the plant matter feedstock comprises corn, wheat, barley or mixtures thereof.

6. The process of claim 5 wherein the plant matter feedstock comprises barley.

7. The process of claim 1 wherein the temperature of the enzymatic hydrolysate is reduced prior to contacting with the polysaccharide enzyme.

8. The process of claim 1 wherein the temperature of the saccharification-fermentation mixture in the SSF zone is from about 25° C. to about 35° C.

9. The process of claim 1 wherein the polysaccharide enzyme comprises a cellulase.

10. The process of claim 1 wherein the polysaccharide enzyme comprises a cellulase and a hemicellulase.

11. The process of claim 1 wherein the yeast comprises a $C_6$ sugar yeast and a $C_5$ sugar yeast.

12. The process of claim 1 wherein the yeast is capable of converting $C_6$ sugars and $C_5$ sugars to ethanol.

13. The process of claim 1 wherein the process further comprises:
   distilling the saccharification-fermentation mixture to separate at least a portion of the ethanol thereby forming: (i) a distillate product comprising ethanol and (ii) a bottoms product comprising whole stillage, and obtaining a modified co-product from the whole stillage wherein the modified co-product has a fiber content of from about 25 wt. % to about 45 wt. % and a protein content of from about 26 wt. % to about 40 wt. %.

14. The process of claim 13 wherein an ethanol yield of from about 200 to about 450 liters ethanol per metric ton of plant matter feedstock is achieved.

15. The process of claim 13 wherein the plant matter feedstock comprises
   (1) barley and the modified feed co-product comprises:
      Protein: 28-35 wt. % dry matter basis
      Fats: 2-10 wt. % dry matter basis
      Fiber: 35-45 wt. % dry matter basis
      Ash: 2-10 wt. % dry matter basis;
   (2) wheat and the modified feed co-product comprises:
      Protein: 30-35 wt. % dry matter basis
      Fats: 2-10 wt. % dry matter basis
      Fiber: 35-40 wt. % dry matter basis
      Ash: 2-10 wt. % dry matter basis; or
   (3) corn and the modified feed co-product comprises:
      Protein: 30-35 wt. % dry matter basis
      Fats: 5-20 wt. % dry matter basis
      Fiber: 30-36 wt. % dry matter basis
      Ash: 2-10 wt. % dry matter basis.

16. The process of claim 13 wherein the process further comprises:
   forming an acidic aqueous medium comprising the whole stillage or derivative thereof and having a pH from about 2 to about 6, wherein the whole stillage or derivative thereof comprises starch and another polysaccharide selected from the group consisting of hemicellulose and cellulose;
   hydrolyzing at least a portion of the starch, the another polysaccharide, or both in the acidic aqueous medium a temperature of at least 85° C.;
   contacting at least a portion of the starch, the another polysaccharide, or both in the acidic aqueous medium with an enzyme selected from the group consisting of a-amylase, cellulase, hemicellulase, and combinations thereof, the enzyme catalyzing enzymatic hydrolysis of at least a portion of the starch, the another polysaccharide, or both into a fermentable sugar;
   contacting the fermentable sugars with a yeast, wherein during a fermentation period at least a portion of the simple sugars derived from the starch and/or the another polysaccharide are converted by fermentation to produce ethanol; and distilling the fermentation mixture to separate at least a portion of the ethanol thereby forming: (i) a secondary distillate product comprising ethanol; and (ii) a secondary bottoms product comprising a secondary whole stillage.

17. The process of claim 16 wherein a secondary modified feed co-product is obtained from the secondary whole stillage.

18. The process of claim 1 wherein the plant matter feedstock comprises a product derived from fermentation of fruit or seeds of an energy crop to produce ethanol, the product selected from the group consisting of whole stillage, thin stillage, condensates of whole stillage, and condensates of thin stillage.

19. The process of claim 1 wherein the acidic aqueous medium comprising the plant matter feed stock is hydrolyzed at a temperature of between about 120° C. and about 160° C.

20. The process of claim 1 wherein the process provides an ethanol yield increase of from 2% to 15% as compared to the yield for a same process for producing ethanol that does not include a polysaccharide enzyme selected from the group consisting of cellulase, hemicellulase, and combinations thereof.

* * * * *